US007858081B2

(12) United States Patent
Bernard et al.

(10) Patent No.: US 7,858,081 B2
(45) Date of Patent: Dec. 28, 2010

(54) IL-15 MUTANTS HAVING AGONISTS/ANTAGONISTS ACTIVITY

(75) Inventors: Jérôme Bernard, Airvault (FR); Ariane Plet, Nantes (FR); Yannick Jacques, Nantes (FR); Catherine Harb, Nantes (FR); Agnès Quemener, Nantes (FR); Erwan Mortier, Nantes (FR)

(73) Assignee: Inserm (Institut National de la Sante et de la Recherche Medicale), Paris (FR)

( * ) Notice: Subject to any disclaimer, the term of this patent is extended or adjusted under 35 U.S.C. 154(b) by 711 days.

(21) Appl. No.: 10/590,734

(22) PCT Filed: Feb. 10, 2005

(86) PCT No.: PCT/EP2005/002367

§ 371 (c)(1),
(2), (4) Date: Aug. 25, 2006

(87) PCT Pub. No.: WO2005/085282

PCT Pub. Date: Sep. 15, 2005

(65) Prior Publication Data

US 2008/0255039 A1  Oct. 16, 2008

(30) Foreign Application Priority Data

Feb. 27, 2004  (EP) .................................. 04290542

(51) Int. Cl.
*A61K 45/00* (2006.01)
(52) U.S. Cl. ....................................... 424/85.2; 530/351
(58) Field of Classification Search ........................ None
See application file for complete search history.

(56) References Cited

U.S. PATENT DOCUMENTS

| 5,552,303 | A * | 9/1996 | Grabstein et al. ......... 435/69.51 |
| 6,177,079 | B1 | 1/2001 | Grabstein et al. |
| 6,451,308 | B1 | 9/2002 | Strom et al. |

OTHER PUBLICATIONS

Sequence search results: sequence alignment between SEQ ID No. 2 of the present application and SEQ ID No. 2 of US5,552,303.*
Bernard et al., The Journal of Biological Chemistry, vol. 279, No. 23, pp. 24313-24322 (Issue of Jun. 4, 2004).
Fehniger et al., Blood, vol. 97, No. 1, pp. 14-32 (Jan. 2001).
Pettit et al., The Journal of Biological Chemistry, vol. 272, No. 4, pp. 2312-2318 (Issue of Jan. 24, 1997).
Grabstein et al., Science, vol. 264, pp. 965-968 (May 13, 1994).
Burton et al., Proc. Natl. Acad. Sci. USA, vol. 91, pp. 4935-4939 (May 1994).
Sprang et al., Current Opinion in Structural Biology, vol. 3, pp. 815-827 (1993).
Carson et al., J. Exp. Med., vol. 180, pp. 1395-1403 (Oct. 1994).
Armitage et al., The Journal of Immunology, vol. 154, pp. 483-490 (1995).
Wilkinson et al., J. Exp. Med., vol. 181, pp. 1255-1259 (Mar. 1995).
Gin et al., The EMBO Journal, vol. 13, No. 12, pp. 2822-2830 (1994).
Anderson et al., The Journal of Biological Chemistry, vol. 270, No. 50, pp. 29862-29869 (Issue of Dec. 15, 1995).
Norman et al., J. Mol. Biol., vol. 219, pp. 717-725 (1991).
Minami et al., Annu. Rev. Immunol., vol. 11, pp. 245-267 (1993).
Giri et al., Journal of Leukocyte Biology, vol. 57, pp. 763-766 (May 1995).
Lehours et al., Eur. Cytokine Netw., vol. 11, No. 2, pp. 207-215 (Jun. 2000).
Johnston et al., Proc. Natl. Acad. Sci. USA, vol. 92, pp. 8705-8709 (Sep. 1995).
Miyazaki et al., Cell, vol. 81, pp. 223-231 (Apr. 21, 1995).
Bulanova et al., The Journal of Immunology, vol. 167, pp. 6292-6302 (2001).
Pereno et al., Oncogene, vol. 19, pp. 5153-5162 (2000).
Bulfone-Paus et al., The FASEB Journal, vol. 13, pp. 1575-1585 (Sep. 1999).
Stevens et al., Am. J. Physiol., vol. 272, pp. G1201-G1208 (1997).
Kennedy et al., J. Exp. Med., vol. 191, No. 5, pp. 771-780 (Mar. 6, 2000).
Lodolce et al., J. Exp. Med., vol. 194, No. 8, pp. 1187-1193 (Oct. 15, 2001).
Li et al., Nature Medicine, vol. 7, No. 1, pp. 114-118 (Jan. 2001).
Fehniger et al., Cytokine & Growth Factor Reviews, vol. 13, pp. 169-183 (2002).
Collins et al., Proc. Natl. Acad. Sci. USA., vol. 85, pp. 7709-7713 (Oct. 1988).
Sauve et al., Proc. Natl. Acad. Sci. USA, vol. 88, pp. 4636-4640 (Jun. 1991).
Shanafelt et al., Nature Biotechnology, vol. 18, pp. 1197-1202 (Nov. 2000).
Zurawski et al., The EMBO Journal, vol. 12, No. 13, pp. 5113-5119 (1993).
Farner et al., Cytokine, vol. 9, No. 5, pp. 316-327 (May 1997).
Weiss et al., The Journal of Immunology, vol. 133, No. 1, pp. 123-128 (Jul. 1984).
Matrisian et al., Proc. Natl. Acad. Sci. USA, vol. 83, pp. 9413-9417 (Dec. 1986).
Blanc et al., Journal of Immunological Methods, vol. 241, pp. 43-59 (2000).
Slootstra et al., Molecular Diversity, vol. 1, pp. 87-96 (1995).
Tejedor et al., Analytical Biochemistry, vol. 127, pp. 143-149 (1982).
Greene et al., Journal of Experimental Medicine, vol. 162, pp. 363-368 (Jul. 1985).
Chang et al., The Journal of Biological Chemistry, vol. 271, No. 23, pp. 13349-13355 (Issue of Jun. 7, 1996).
Black, Science, vol. 245, pp. 486-493 (Aug. 4, 1989).
Bamborough et al., Structure, vol. 2, pp. 839-851 (Sep. 15, 1994).
Chae D-W et al., "Mutant IL-15 protein exerting antagonistic effects on IL-15 triggered cell proliferation" (Sep. 1996) (Abstract A 2029).

* cited by examiner

*Primary Examiner*—Dong Jiang
(74) *Attorney, Agent, or Firm*—Birch, Stewart, Kolasch & Birch, LLP

(57) ABSTRACT

The present invention relates to the identification of an epitope in human Interleukin-15 (IL-15) that is responsible for binding to the interleukin-15 receptor α-chain. Two IL-15 regions are involved in the formation of this epitope: the first region ($_{44}$LLELQVISL$_{52}$, peptide 1) corresponds to a sequence located in the B helix and the second ($_{64}$ENLIL$_{68}$, peptide 2 or $_{64}$ENLIIL$_{69}$, peptide 2a) to a sequence located in helix C. Muteins displaying agonist or antagonist properties are described, and may be useful as therapeutic agents.

15 Claims, 25 Drawing Sheets

```
  1 gactccggt ggcaggcgcc cggggaatc ccagctgact cgctcactgc cttcgaagtc
 61 cggcgcccc cgggagggaa ctgggtggcc gcaccctccc ggctgcggtg gctgtcgccc
121 cccaccctgc agccaggact cgatggagaa tccattccaa tatatggcca tgtggctctt
181 tggagcaatg ttccatcatg ttccatgctg ctgctgacgt cacatggagc acagaaatca
241 atgttagcag atagcagcc catacaagat cgtattgtat tgtaggaggc atcgtggatg
301 gatggctgct ggaaacccct tgccatagcc agctctctt caatacttaa ggattaccg
361 tggctttgag taatgagaat ttcgaaacca catttgagaa gtatttccat ccagtgctac
421 ttgtgttac ttctaaacag tcatttctta actgaagctg gcattcatgt cttcattttg
481 ggctgttca gtgcagggct tcctaaaaca gaagccaact gggtgaatgt aataagtgat
541 ttgaaaaaa ttgaagatct tattcaatct atgcatatct atgctacttt atatacggaa
601 agtgatgttc accccagttg caaagtaaca gcaatgaagt gctttctctt ggagttacaa
661 gttatttcac ttgagtccgg agatgcaagt attcatgata cagtagaaaa tctgatcatc
721 ctagcaaaca acagtttgtc ttctaatggg aatgtaacag aatctggatg caaagaatgt
781 gaggaactgg aggaaaaaaa tattaaagaa tttttgcaga gttttgtaca tattgtccaa
841 atgttcatca acacttcttg attgcaattg attctttta aagtgtttct gttattaaca
901 aacatcactc tgctgcttag acataacaaa acactcggca tttcaaatgt gctgtcaaaa
961 caagttttc tgtcaagaag atgatcagac cttggatcag atgaactctt agaaatgaag
1021 gcagaaaaat gtcattgagt aatatagtga ctatgaactt ctctcagact tactttactc
1081 attttttaa tttattattg aaattgtaca tatttgtgga ataatgtaaa atgttgaata
1141 aaaatatgta caagtgttgt ttttaagtt gcactgatat tttacctctt attgcaaaat
1201 agcatttgtt taagggtgat agtcaaatta tgtattggtg gggctgggta ccaatgctgc
1261 aggtcaacag ctatgctggt aggctcctgc cagtgtggaa ccactgacta ctggctctca
1321 ttgacttcct tactaagcat agcaaacaga ggaagaattt gttatcagta agaaaagaa
1381 gaactatatg tgaatcctct tctttatact gtaatttagt tattgatgta taaagcaact
1441 gttatgaaat aaagaaattg caataactgg caaaaaaaaa aaaaaaaaaa aaaaaa
```

SEQ ID NO :1   Human IL-15 wild-type mature IL-15 (CDS from 373 to 861)

FIGURE 1A

1   NWVNVISDLK   KIEDLIQSMH   IDATLYTESD
                     44          52
31  VHPSCKVTAM   KCFLLELQVI   SLESGDASIH
       64  69
61  DTVENLIILA   NNSLSSNGNV   TESGCKECEE

91  LEEKNIKEFL   QSFVHIVQMF   INTS

Human wild-type mature IL-15 amino acids 49 to 162 of SEQ ID NO:2

FIGURE 1A (end)

peptide 1:

```
            646                                    672
            ctc ttg gag tta caa gtt att tca ctt          SEQ ID NO: 3
                 45                        51 52
                 L  L  E  L  Q  V  I  S  L            SEQ ID NO: 4
``` peptide 2:

```
            706                              720
            gaa aat ctg atc atc                      SEQ ID NO: 5
                 64 65        68
                 E  N  L  I  I                        SEQ ID NO: 6
``` peptide 2a:

```
            706                                  723
            gaa aat ctg atc atc cta                  SEQ ID NO: 66
                 64 65           69
                 E  N  L  I  I  L                    SEQ ID NO: 67
```

FIGURE 1B

```
                    45            51 52
peptide 1 :    L  L  E  L  Q  V  I  S  L         SEQ ID NO :4
----------------------------mutant peptides----------------------------

L  D  E  L  Q  V  I  S  L         SEQ ID NO :7

L  E  E  L  Q  V  I  S  L         SEQ ID NO :8

L  K  E  L  Q  V  I  S  L         SEQ ID NO :9

L  R  E  L  Q  V  I  S  L         SEQ ID NO :10

L  L  E  L  Q  V  I  D  L         SEQ ID NO :11

L  L  E  L  Q  V  I  E  L         SEQ ID NO :12

L  L  E  L  Q  V  I  K  L         SEQ ID NO :13

L  L  E  L  Q  V  I  R  L         SEQ ID NO :14

L  L  E  L  Q  V  I  S  D         SEQ ID NO :15

L  L  E  L  Q  V  I  S  E         SEQ ID NO :16

L  L  E  L  Q  V  I  S  K         SEQ ID NO :17

L  L  E  L  Q  V  I  S  R         SEQ ID NO :18
```

Figure 2A

|            | 64 65   68 |              |
|------------|------------|--------------|
| peptide 2 :| E N L I I  | SEQ ID NO :6 |

------------------------------mutant peptides------------------------------

|   |           |               |
|---|-----------|---------------|
|   | K N L I I | SEQ ID NO :19 |
|   | R N L I I | SEQ ID NO :20 |
|   | E D L I I | SEQ ID NO :21 |
|   | E E L I I | SEQ ID NO :22 |
|   | E K L I I | SEQ ID NO :23 |
|   | E R L I I | SEQ ID NO :24 |
|   | E N L I D | SEQ ID NO :25 |
|   | E N L I E | SEQ ID NO :26 |
|   | E N L I K | SEQ ID NO :27 |
|   | E N L I R | SEQ ID NO :28 |

Figure 2B

```
 1  NWVNVISDLK  KIEDLIQSMH  IDATLYTESD

31  VHPSCKVTAM  KCFLDELQVI  SLESGDASIH

61  DTVENLIILA  NNSLSSNGNV  TESGCKECEE

91  LEEKNIKEFL  QSFVHIVQMF  INTS
```

L45D SEQ ID NO :29

```
 1  NWVNVISDLK  KIEDLIQSMH  IDATLYTESD

31  VHPSCKVTAM  KCFLEELQVI  SLESGDASIH

61  DTVENLIILA  NNSLSSNGNV  TESGCKECEE

91  LEEKNIKEFL  QSFVHIVQMF  INTS
```

L45E SEQ ID NO :30

FIGURE 2C

```
 1  NWVNVISDLK  KIEDLIQSMH  IDATLYTESD

31  VHPSCKVTAM  KCFLKELQVI  SLESGDASIH

61  DTVENLIILA  NNSLSSNGNV  TESGCKECEE

91  LEEKNIKEFL  QSFVHIVQMF  INTS
```

L45K SEQ ID NO :31

```
 1  NWVNVISDLK  KIEDLIQSMH  IDATLYTESD

31  VHPSCKVTAM  KCFLRELQVI  SLESGDASIH

61  DTVENLIILA  NNSLSSNGNV  TESGCKECEE

91  LEEKNIKEFL  QSFVHIVQMF  INTS
```

L45R SEQ ID NO :32

FIGURE 2C (continued)

```
 1   NWVNVISDLK   KIEDLIQSMH   IDATLYTESD
31   VHPSCKVTAM   KCFLLELQVI   DLESGDASIH
61   DTVENLIILA   NNSLSSNGNV   TESGCKECEE
91   LEEKNIKEFL   QSFVHIVQMF   INTS
```

S51D SEQ ID NO :33

```
 1   NWVNVISDLK   KIEDLIQSMH   IDATLYTESD
31   VHPSCKVTAM   KCFLLELQVI   ELESGDASIH
61   DTVENLIILA   NNSLSSNGNV   TESGCKECEE
91   LEEKNIKEFL   QSFVHIVQMF   INTS
```

S51E SEQ ID NO :34

FIGURE 2C (continued)

```
 1  NWVNVISDLK  KIEDLIQSMH  IDATLYTESD
31  VHPSCKVTAM  KCFLLELQVI  KLESGDASIH
61  DTVENLIILA  NNSLSSNGNV  TESGCKECEE
91  LEEKNIKEFL  QSFVHIVQMF  INTS
```

S51K SEQ ID NO :35

```
 1  NWVNVISDLK  KIEDLIQSMH  IDATLYTESD
31  VHPSCKVTAM  KCFLLELQVI  RLESGDASIH
61  DTVENLIILA  NNSLSSNGNV  TESGCKECEE
91  LEEKNIKEFL  QSFVHIVQMF  INTS
```

S51R SEQ ID NO :36

FIGURE 2C (continued)

```
 1  NWVNVISDLK  KIEDLIQSMH  IDATLYTESD

31  VHPSCKVTAM  KCFLLELQVI  SDESGDASIH

61  DTVENLIILA  NNSLSSNGNV  TESGCKECEE

91  LEEKNIKEFL  QSFVHIVQMF  INTS
```

L52D SEQ ID NO :37

```
 1  NWVNVISDLK  KIEDLIQSMH  IDATLYTESD

31  VHPSCKVTAM  KCFLLELQVI  SEESGDASIH

61  DTVENLIILA  NNSLSSNGNV  TESGCKECEE

91  LEEKNIKEFL  QSFVHIVQMF  INTS
```

L52E SEQ ID NO :38

FIGURE 2C (continued)

```
 1  NWVNVISDLK   KIEDLIQSMH   IDATLYTESD
31  VHPSCKVTAM   KCFLLELQVI   SKESGDASIH
61  DTVENLIILA   NNSLSSNGNV   TESGCKECEE
91  LEEKNIKEFL   QSFVHIVQMF   INTS
```

L52K SEQ ID NO :39

```
 1  NWVNVISDLK   KIEDLIQSMH   IDATLYTESD
31  VHPSCKVTAM   KCFLLELQVI   SRESGDASIH
61  DTVENLIILA   NNSLSSNGNV   TESGCKECEE
91  LEEKNIKEFL   QSFVHIVQMF   INTS
```

L52R SEQ ID NO :40

FIGURE 2C (end)

```
 1  NWVNVISDLK  KIEDLIQSMH  IDATLYTESD

31  VHPSCKVTAM  KCFLLELQVI  SLESGDASIH

61  DTVKNLIILA  NNSLSSNGNV  TESGCKECEE

91  LEEKNIKEFL  QSFVHIVQMF  INTS
```

E64K SEQ ID NO :41

```
 1  NWVNVISDLK  KIEDLIQSMH  IDATLYTESD

31  VHPSCKVTAM  KCFLLELQVI  SLESGDASIH

61  DTVRNLIILA  NNSLSSNGNV  TESGCKECEE

91  LEEKNIKEFL  QSFVHIVQMF  INTS
```

E64R SEQ ID NO :42

FIGURE 2D

```
 1  NWVNVISDLK  KIEDLIQSMH  IDATLYTESD

31  VHPSCKVTAM  KCFLLELQVI  SLESGDASIH

61  DTVEDLIILA  NNSLSSNGNV  TESGCKECEE

91  LEEKNIKEFL  QSFVHIVQMF  INTS
```

N65D SEQ ID NO :43

```
 1  NWVNVISDLK  KIEDLIQSMH  IDATLYTESD

31  VHPSCKVTAM  KCFLLELQVI  SLESGDASIH

61  DTVEELIILA  NNSLSSNGNV  TESGCKECEE

91  LEEKNIKEFL  QSFVHIVQMF  INTS
```

N65E SEQ ID NO :44

FIGURE 2D (continued)

```
  1  NWVNVISDLK  KIEDLIQSMH  IDATLYTESD

31  VHPSCKVTAM  KCFLLELQVI  SLESGDASIH

61  DTVEKLIILA  NNSLSSNGNV  TESGCKECEE

91  LEEKNIKEFL  QSFVHIVQMF  INTS
```

N65K SEQ ID NO :45

```
  1  NWVNVISDLK  KIEDLIQSMH  IDATLYTESD

31  VHPSCKVTAM  KCFLLELQVI  SLESGDASIH

61  DTVERLIILA  NNSLSSNGNV  TESGCKECEE

91  LEEKNIKEFL  QSFVHIVQMF  INTS
```

N65R SEQ ID NO :46

FIGURE 2D (continued)

```
 1  NWVNVISDLK  KIEDLIQSMH  IDATLYTESD
31  VHPSCKVTAM  KCFLLELQVI  SLESGDASIH
61  DTVENLIDLA  NNSLSSNGNV  TESGCKECEE
91  LEEKNIKEFL  QSFVHIVQMF  INTS
```

I68D SEQ ID NO :47

```
 1  NWVNVISDLK  KIEDLIQSMH  IDATLYTESD
31  VHPSCKVTAM  KCFLLELQVI  SLESGDASIH
61  DTVENLIELA  NNSLSSNGNV  TESGCKECEE
91  LEEKNIKEFL  QSFVHIVQMF  INTS
```

I68E SEQ ID NO :48

FIGURE 2D (continued)

```
  1  NWVNVISDLK   KIEDLIQSMH   IDATLYTESD
 31  VHPSCKVTAM   KCFLLELQVI   SLESGDASIH
 61  DTVENLIKLA   NNSLSSNGNV   TESGCKECEE
 91  LEEKNIKEFL   QSFVHIVQMF   INTS
```

I68K SEQ ID NO :49

```
  1  NWVNVISDLK   KIEDLIQSMH   IDATLYTESD
 31  VHPSCKVTAM   KCFLLELQVI   SLESGDASIH
 61  DTVENLIRLA   NNSLSSNGNV   TESGCKECEE
 91  LEEKNIKEFL   QSFVHIVQMF   INTS
```

I68R SEQ ID NO :50

FIGURE 2D (end)

|  | 64 | 65 |  | 68 | 69 |  |
|---|---|---|---|---|---|---|
| peptide 2 : | E | N | L | I | I | L | SEQ ID NO :67 |

------mutant peptides------

| | | | | | | |
|---|---|---|---|---|---|---|
| K | N | L | I | I | L | SEQ ID NO :68 |
| R | N | L | I | I | L | SEQ ID NO :69 |
| E | D | L | I | I | L | SEQ ID NO :70 |
| E | E | L | I | I | L | SEQ ID NO :71 |
| E | K | L | I | I | L | SEQ ID NO :72 |
| E | R | L | I | I | L | SEQ ID NO :73 |
| E | N | L | I | D | L | SEQ ID NO :74 |
| E | N | L | I | E | L | SEQ ID NO :75 |
| E | N | L | I | K | L | SEQ ID NO :76 |
| E | N | L | I | I | D | SEQ ID NO :77 |
| E | N | L | I | I | E | SEQ ID NO :78 |
| E | N | L | I | I | K | SEQ ID NO :79 |
| E | N | L | I | I | R | SEQ ID NO :80 |
| E | N | L | I | R | L | SEQ ID NO :81 |

FIGURE 9

1   NWVNVISDLK   KIEDLIQSMH   IDATLYTESD

31  VHPSCKVTAM   KCFLLELQVI   SLESGDASIH

61  DTVENLIIDA   NNSLSSNGNV   TESGCKECEE

91  LEEKNIKEFL   QSFVHIVQMF   INTS

L69D SEQ ID NO :82

1   NWVNVISDLK   KIEDLIQSMH   IDATLYTESD

31  VHPSCKVTAM   KCFLLELQVI   SLESGDASIH

61  DTVENLIIEA   NNSLSSNGNV   TESGCKECEE

91  LEEKNIKEFL   QSFVHIVQMF   INTS

L69E SEQ ID NO :83

FIGURE 10

```
1   NWVNVISDLK   KIEDLIQSMH   IDATLYTESD

31  VHPSCKVTAM   KCFLLELQVI   SLESGDASIH

61  DTVENLIIKA   NNSLSSNGNV   TESGCKECEE

91  LEEKNIKEFL   QSFVHIVQMF   INTS
```

<u>L69K SEQ ID NO :84</u>

```
1   NWVNVISDLK   KIEDLIQSMH   IDATLYTESD

31  VHPSCKVTAM   KCFLLELQVI   SLESGDASIH

61  DTVENLIIRA   NNSLSSNGNV   TESGCKECEE

91  LEEKNIKEFL   QSFVHIVQMF   INTS
```

<u>L69R SEQ ID NO :85</u>

<u>FIGURE 10 (end)</u>

IL-15 MUTANTS HAVING AGONISTS/ANTAGONISTS ACTIVITY

FIELD OF THE INVENTION

The present invention describes the identification of a human IL-15 binding site for IL-15Ralpha. It also provides IL-15 agonists and antagonists that target the IL-15Ralpha chain, i.e. the chain that confers to the IL-15R receptor complex its specificity for IL-15.

In the present application, reference is made to various scientific publications. These publications are listed at the end of the example part, before the claims. Reference thereto is made in the application text by way of a number between parentheses; this number corresponds to the number in the publication list.

TECHNICAL BACKGROUND

Interleukin-15 (IL-15) was identified as a new cytokine able to replace IL-2 in supporting the proliferation of a murine T cell line (1, 2). Both cytokines belong to the four alpha helix bundle family (3). IL-15 was initially found to mimic most of the in vitro activities elicited by IL-2 in vitro, including induction of proliferation and cytotoxicity by activated T cells (1) and NK cells (2, 4), co-stimulation of B cell proliferation and immunoglobulin synthesis (5) and chemo-attraction for T cells (6). This redundancy is explained by the common usage within their functional receptors of the IL-2Rβ/γ signaling complex. This IL-2Rβ/γ complex is a common intermediate affinity receptor for IL-2 and IL-15 (Kd=1 nM), and both cytokines compete to bind to this receptor (7). Cytokine specificity is conferred by additional private chains, IL-2Rα and IL-15Rα, that are structurally related (8). These two chains contain structural domains (called sushi domains) previously found in some complement and adhesion molecules (9). IL-2Rα contains two such domains, whereas IL-15Rα contains only one. One noticeable difference is that IL-2 binds to its specific IL-2Rα with an affinity (Kd=10 nM) far lower than IL-15 to IL-15Rα (d=0.05 nM). Each specific chain can associate with the IL-2Rβ/γ complex to form a cytokine-specific, functional high-affinity (αβγ) receptor (10-12). Due to the sharing of this IL-2Rβ/γ complex, both cytokines trigger similar downstream signaling pathways including activation of Jak-1/Jak-3 tyrosine kinases and subsequent nuclear translocation of the phosphorylated Stat-3 and Stat-5, activation of Lck and Syk tyrosine kinases, activation of the MAP kinase pathway, and induction of Bcl-2 (13, 14). In contrast to IL-2Rβ and IL-2Rγ that are required for signal transduction, the specific receptors IL-2Rα and IL-15Rα have short intracellular tails (13 and 41 amino-acids respectively) and IL-2Rα is considered to play no role in signal transduction. While initial studies have pointed out the dispensable role of the intracellular tail of IL-15Rα in signaling (8), more recent data suggest that IL-15Rα might mediate certain intracellular functions (15-17).

In contrast to the general functional redundancy observed in vitro, several findings point to complementary and even opposing actions of IL-2 and IL-15 in vivo. Indeed, whereas IL-2 and IL-2Rα gene expression is mainly restricted to the activated T cell compartment, IL-15 and IL-15Rα transcripts are expressed by various cell types and tissues (monocytes, dendritic and stromal cells, keratinocytes, placenta, skeletal muscle, heart) suggesting additional roles for the IL-15 system beyond the immune system (7, 8). Cells expressing IL-15Rα in the absence of IL-2Rβ and/or IL-2Rγ have been described and some of them respond to IL-15 (17, 18), suggesting the existence of new functional IL-15 receptor complexes not involving IL-2Rβ and/or IL-2Rγ.

Distinct roles for IL-2 and IL-15 are also suggested from experiments in knock-out mice. While IL-2$^{-/-}$ and IL-2Rα$^{-/-}$ mice develop exacerbated T and B cell expansion associated with autoimmune manifestations, IL-15$^{-/-}$ and IL-15Rα$^{-/-}$ mice on the contrary have normal T and B cell populations and display a profound defect in NK cells, NK-T cells, intraepithelial lymphocytes and CD8$^+$ memory T cells (19, 20). A recent study suggests that, contrary to the results obtained in vitro, the major role of IL-2 in vivo is to limit continuous expansion of activated T cells, whereas IL-15 is critical for initiating T cell division (21).

A number of studies have contributed to the identification of human disorders in which targeting the IL-15 system is of clinical relevance and potential benefit. Among them are autoimmune and inflammatory diseases, infectious diseases, transplant rejection, cancer and immunodeficiencies (22, 23). In this context, the rational design of agonists or antagonists of the IL-15/receptor system is a major concern and requires a precise knowledge of the structure of the high-affinity IL-15 receptor complex.

A number of mutagenesis studies of human and murine IL-2 have led to the identification of several residues implicated in the binding to the IL-2Rα, β and γ chains. From these studies, residues K35, R38, F42 and K43, all located in the A-B loop of human IL-2, are involved in its binding to the IL-2Rα chain, whereas residues D20 on helix A and N88 on helix C are involved in the binding to the IL-2Rβ chain, and Q126 on helix D is crucial for binding to the IL-2Rγ chain (24-26). Similar regions were identified on mouse IL-2 (27).

On the contrary, very little data is available concerning the residues on IL-15 involved in the binding to the different IL-15 receptors.

Some mutations in human IL-15 (D8 and Q108) which are analogous to the ones described for human IL-2 suggested that the corresponding regions in IL-15 are involved in the binding to the IL-2Rβ and γ subunits, respectively (28).

The present invention follows different complementary approaches including ligand receptor interaction analysis, induction of biological activity, peptide scanning, and site-directed mutagenesis, to define the epitope of IL-15 responsible for high-affinity binding to the IL-15Rα chain.

SUMMARY OF THE INVENTION

The present invention provides with an epitope of human IL-15 responsible for high-affinity binding to the IL-15Rα chain. This IL-15/IL15-Ralpha epitope essentially consists in two peptides: peptide 1 ($_{44}$LLELQVISL$_{52}$; SEQ ID NO:4 on FIG. 1B) which is located in IL-15 helix B, and peptide 2 ($_{64}$ENLII$_{68}$; SEQ ID NO:6 on FIG. 1B) or peptide 2a ($_{64}$ENLIIL$_{69}$; SEQ ID NO:67 on FIG. 1B) which are located in helix C. In the present application, all residue numbers are computed by reference to the full sequence of the mature human IL-15 protein (SEQ ID NO:2 shown on FIG. 1A). Peptide 1 and peptide 2 or 2a together configure in an epitopic surface that is responsible for high-affinity binding of IL-15 to IL-15Rα. Peptides 2 and 2a are also involved in the recruitment of the IL-2Rβ transducing subunit.

The present invention also provides IL-15 agonists and antagonists, and more particularly IL-15 agonists and antagonists which derive from said epitopic peptides by mutation (see FIGS. 2A, 2B, 2C, 2D, 9, 10).

Preferred agonists include those muteins wherein at least one of L45, S51 and L52 have been replaced by a charged group (D, E, R or K); see FIGS. 2A and 2C. A particularly preferred agonist comprises L45 replaced by D or E, and/or S51 replaced by D, and/or L52 replaced by D: these IL-15 muteins display binding and biological properties higher than those of wild-type IL-15, and thus behave as super-agonists. They are particularly valuable tools to expand lymphocyte subsets (e.g. NK cells, NK-T cells, CD8+ memory T cells) and are useful as therapeutic agents in patients with cancer or immunodeficiencies.

Preferred antagonists include those muteins wherein at least one of E64, I68, L69 and N65 have been replaced by an oppositely charged group (K or R) or by charged group (D, E, R or K); see FIGS. 2B and 2D. A particularly preferred antagonist comprises N65 mutated by a charged group (D, E, R or K), such as K. These muteins are antagonist or potential antagonists, and might therefore be useful in inflammatory conditions or diseases like rheumatoid arthritis and generalized Shwartzman reaction where IL-15 is thought to play an important role (22).

The present invention also relates to a process for the production of IL-15 muteins, to the nucleic acids coding for these muteins, to the transfection vectors and host cells containing such a nucleic acid, as well as to a method for screening for IL-15 agonist and antagonist.

Biological or medical applications of these epitopic peptides and muteins, such as drugs containing such muteins, also fall within the scope of the present invention.

DESCRIPTION OF THE FIGURES

FIG. 1A shows:
the human IL-15 gene sequence (SEQ ID NO:1), and the CDS start and stop positions thereof,
the sequence of the human mature IL-15 protein (amino acids 49-162 of SEQ ID NO:2); peptide 1 (from L44 to L52), peptide 2 (from E64 to I68) and peptide 2a (from E64 to L69) are shown in bold characters,
FIG. 1B shows the DNA and aminoacid sequences of peptide 1 L44-L52 (SEQ ID NO:3 and SEQ ID NO:4, respectively), and the DNA and aminoacid sequences of peptide 2 E64-I68 (SEQ ID NO:5 and SEQ ID NO:6, respectively), and the DNA and aminoacid sequences of peptide 2a E64-L69 (SEQ ID NO:66 and SEQ ID NO:67, respectively),
FIG. 2A shows the sequence of peptide 1 (L44-L52; SEQ ID NO:4), and some muteins deriving therefrom that have IL-15 agonist activity (SEQ ID NO:7-18),
FIG. 2B shows the sequence of peptide 2 (E64-I68; SEQ ID NO:6), and some muteins deriving therefrom (SEQ ID NO: 19-28) that are IL-15 antagonist or partial agonists,
FIG. 2C shows the sequence of some IL-15 muteins of the invention, which derives from human mature wild-type IL-15 by substitution of residue 45 (SEQ ID NO:29-32), or of residue 51 (SEQ ID NO:33-36), or of residue 52 (SEQ ID NO:37-40),
FIG. 2D shows the sequence of some IL-15 muteins of the invention, which derives from human mature wild-type IL-15 by substitution of residue 64 (SEQ ID NO:41-42), or of residue 65 (SEQ ID NO:43-46), or of residue 68 (SEQ ID NO:47-50)

FIG. 3A: twelve-mer peptides spanning the entire aminoacid sequence of human IL-15 were immobilized in multiwell plates, and tested for their reactivity with the different molecules as indicated. The left side of each sub-panel corresponds to the N-terminal 12-mer peptide of IL-15. The sIL-15Rα-IL-2 fusion protein (20 μg/ml, i.e. 330 nM) or rIL-2 (5 μg/ml, i.e. 330 nM) were incubated and their binding revealed with the goat AF-202-NA anti-human IL-2 antibody plus a peroxidase-coupled rabbit anti-goat IgG. The reactivity of each well (ordinates, arbitrary scale) is measured as described in experimental procedures.

FIG. 3B: the peptide regions of human IL-15 recognized by sIL-15Rα-IL-2 are positioned on the primary structure of IL-15. The four alpha helices are shown.

FIG. 4A: WT (■), L45D (♦), L45E (◊), E46K (σ)

FIG. 4B: WT (■) Q48K (□), V49D (♦), I50D (◊), S51D (σ), L52D (Δ)

FIG. 4C: WT (■), E64K (□), N65K (♦), L66D (◊), L66E (σ), I67D (Δ), I67E (●), I68D (○),

FIG. 5A: WT (■), L44D (□), L45D (♦), L45E (◊), E46K (σ), L47D (Δ),

FIG. 5B: WT (■) Q48K (□), V49D (♦), I50D (◊), S51D (σ), L52D (Δ),

FIG. 5C: WT (■), E64K (□), N65K (♦), L66D (◊), L66E (σ), I67D (Δ), I67E (●), I68D (○),

FIG. 9 shows the sequence of peptide 2a (E64-L69; SEQ ID NO:67), and some muteins deriving therefrom (SEQ ID NO:68-81) that are IL-15 antagonist candidates (partial agonists), FIG. 10 shows the sequence of some IL-15 muteins of the invention, which derives from human mature wild-type IL-15 by substitution of residue 69 (SEQ ID NO:82-85).

DETAILED DESCRIPTION OF THE INVENTION

Figures 3A, 3B:
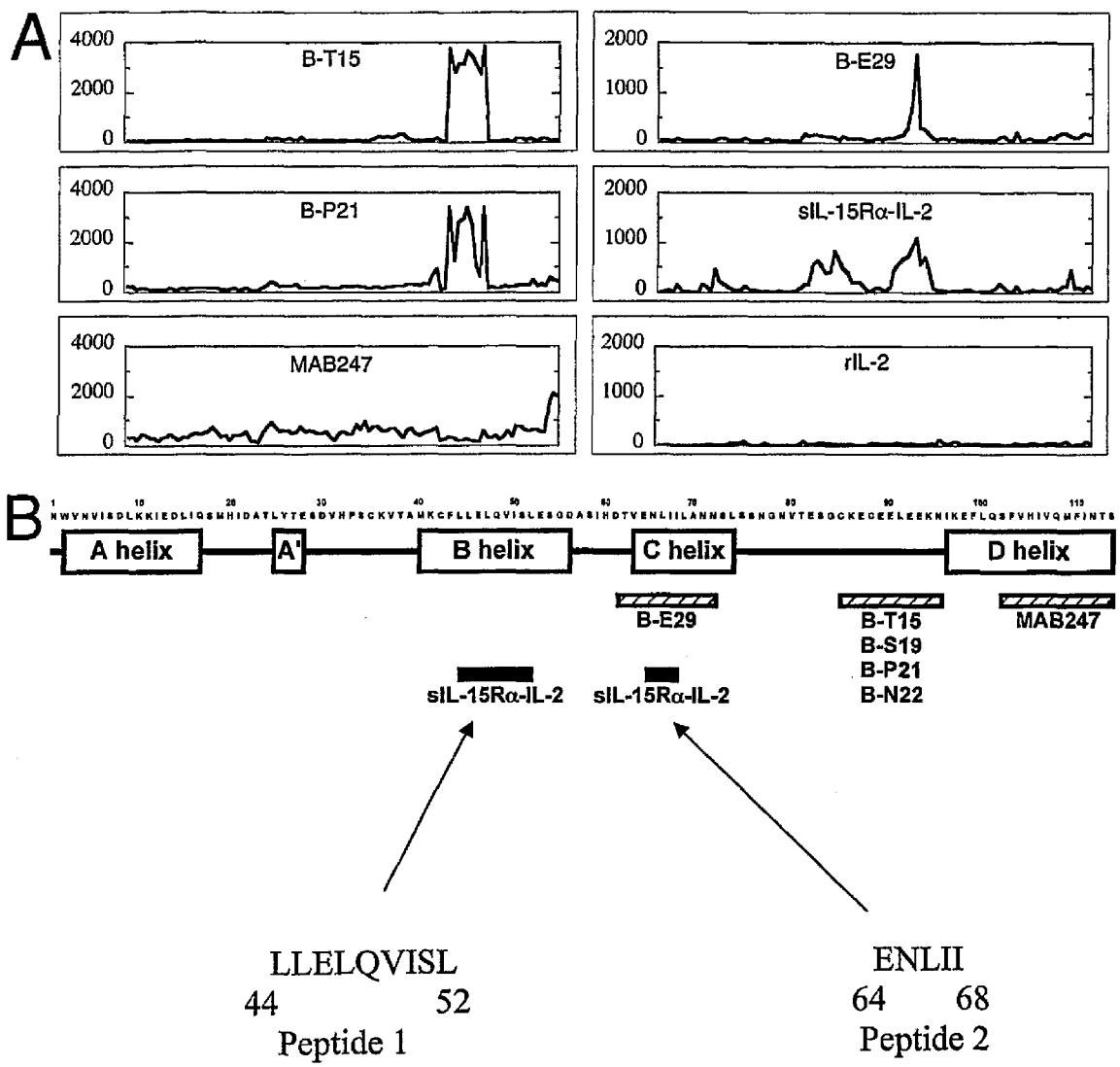
FIGS. 3A and 3B illustrate the analysis of the binding of sIL-15Rα-IL-2 to IL-15 12-mer peptides.

The present invention describes the identification of an epitope in IL-15 that is responsible for high-affinity binding to the IL-15Ralpha chain. This epitope is essentially formed by two peptides: peptide 1 of SEQ ID NO:4, and peptide 2 of SEQ ID NO:6 or peptide 2a of SEQ ID NO:67 (see FIG. 1B). In human mature wild-type IL-15, peptide 1 is located in helix B; peptide 2 and peptide 2a are located in helix C (see FIG. 3B).

Site-directed mutagenesis of peptide 1 and peptides 2 and 2a show that these peptides are involved in IL-15Ralpha binding.

Surprisingly, mutations at positions L45, S51 and L52 (peptide 1) did not result in reduction but in an increase in binding and bio-activity, such that the resulting mutants behave as super-agonists. They are valuable tools to expand lymphocyte subsets (e.g. NK cells, NK-T cells, CD8+ memory T cells), and may be useful as therapeutic agents in patients with cancer or immunodeficiencies.

Site-directed mutagenesis of peptides 2 and 2a shows that peptide 2 and 2a participate both in IL-15Ralpha and IL-2Rbeta binding, and that all aminoacids of peptides 2 and 2a (E64 to I68 and L69) are involved in this process. L66 and I67 are apparently more particularly involved in IL-15 binding to IL-15Ralpha, whereas E64, N65, I68, and L69 are apparently more particularly involved in the recruitment of IL-15Rbeta. Mutations at positions E64, N65, I68 and L69 induce properties that designate the resulting mutants as potential IL-15 antagonists; more particularly, they behave as IL-15 antagonist (N65) or partial agonists (E64, I68, L69). They may be useful in inflammatory diseases like rheumatoid arthritis and generalised Shwartzman reaction.

Compounds interfering with the binding of these IL-15 epitopic peptides to IL-15Ralpha may act as IL-15 agonist or antagonist. As this IL-15Ralpha chain is the subunit that confers the specificity of the IL-15R receptor complex for IL-15 compared to IL-2, such agonists and antagonists are particularly advantageous in terms of specificity. The present application is directed to such agonistic and antagonistic compounds, and notably describes muteins having such agonistic or antagonistic effects.

The terms agonist and antagonist are herein given their ordinary meaning in the field.

A compound is termed IL-15 agonist when it induces a biological response that is of a similar or higher level than the one induced by native IL-15. Preferred agonists are those which induce an even higher level of biological response (super-agonist).

An IL-15 agonist typically has an affinity for binding to IL-15Ralpha that is at least not significantly different from the one of native IL-15, and that is preferably significantly higher than the one of native IL-15.

An antagonist interferes with the binding of IL-15 to its target receptor or receptor chain, such that it antagonizes IL-15's biological activity. More particularly, a compound is termed IL-15 antagonist when it can compete with native IL-15 for binding to its IL-15Ralpha and/or IL15-Rbeta and/or IL-15-Rgamma receptor chain target, and to thereupon either block or significantly inhibit the biological response induced by said native IL-15. Partial agonists are hence herein encompassed within the term "antagonist". Antagonist candidates are those compounds that have an affinity for binding to IL-15Ralpha and/or IL-15Rbeta and/or IL-15-Rgamma that is either not significantly different from, or higher than the one of native IL-15, and that induce no, or a significantly lower level of biological response than native IL-15.

Said biological response is a biological response induced by IL-15. The skilled person can choose any IL-15 inducible biological response that he/she finds appropriate or convenient to assess or monitor.

Typical IL-15 inducible biological response are proliferation of IL-15 sensitive cells, such as e.g. CTL-L2 mouse cytotoxic T lymphoma cell line (ATCC accession number TIB-214), or TF1-beta cells.

TF-1 cells are available from the American Type Culture Collection ATCC; 10801 University Blvd.; Manassas, Va. 20110-2209; U.S.A.; under ATCC accession number CRL-2003. Beta chain templates are available from RNA of HuT102 (ATCC TIB-162) or Jurkat clone E6.1 (ATCC TIB 152) by RT-PCR using the proofreading polymerase Pfu (Stratagene no 600390) and 5'GAGAGACTGGATGGACCC 3' as sense primer (SEQ ID NO:51), and 5' AAGAAAC-TAACTCTTAAAGAGGC3' as anti-sense primer (SEQ ID NO:52) according to human IL-2R beta sequence (NCBI accession number K03122). The PCR product is efficiently cloned using the Zero Blunt PCR Cloning Kit (In Vitrogen cat no K2700-20) or the TOPO XL PCR cloning kit (In Vitrogen cat no K4750-10). The cDNA for IL-2R beta gene is then subcloned into the multiple cloning site of the pLXRN retrovirus expression vector of the Pantropic Retroviral Expression System (BD Biosciences Clontech no 631512) and transfected into GP2-293 cells, as described in the kit to generate recombinant retroviruses. IL-2R beta recombinant retroviruses can then be used to infect TF-1 cells to generate TF-10 after selection in medium containing G418.

The skilled person may alternatively choose to assess or monitor an IL-15 biological response that is more downstream in the signalling pathway, such as activation of a tyrosine kinase (e.g. Jak-1/Jak-3; Lck; Syk), activation of a MAP kinase, or a nuclear translocation event (e.g. translocation of phosphorylated Stat-3 and/or Stat-5). The biological response may then be an acellular response.

The present application thus relates to three peptides that are part of the epitope in human IL-15 that is responsible for high-affinity binding of IL-15 to the IL-15Ralpha chain. They respectively have the sequence of the region of human mature wild-type IL-15 from L44 to L52 (SEQ ID NO:4), or the sequence of the region of human mature wild-type IL-15 from E64 to I68 (SEQ ID NO:6), or the sequence of the region of human mature wild-type IL-15 from E64 to L69 (SEQ ID NO:67); see FIG. 1B.

Nucleic acids (DNA or RNA) coding for such an epitopic peptide are also encompasses within the scope of the present invention. Exemplary nucleic acids includes those of SEQ ID NO:3, SEQ ID NO:5 and SEQ ID NO:66 (see FIG. 1B).

Methods to produce antibodies that bind to a given peptide or protein are well known to those skilled in the art, see e.g. "*Antibodies: a laboratory manual*"/edited by Ed Harlow, David Lane, publisher Cold Spring Harbor Laboratory, 1988. Also routinely achieved is the production of monoclonal antibodies, see e.g. the hybridoma technique described in Köhler and Milstein 1975, Nature 256:495-497.

These methods can be used for the production of antibodies, more particularly monoclonal antibodies, which bind to an epitopic peptide and/or a mutein of the invention.

A variety of immunoassay formats may be used to select antibodies specifically immunoreactive with a particular protein. For example, solid-phase ELISA immunoassays are routinely used to select antibodies specifically immunoreactive with a protein, see e.g. "*Antibodies: a laboratory manual*" (edited by Ed Harlow, David Lane, publisher Cold Spring Harbor Laboratory, 1988), for a description of immunoassay formats and conditions that can be used to determine specific immunoreactivity. Antibodies or monoclonal antibodies with a defined specificity can thus be produced.

Advantageous anti-IL15 antibodies or monoclonal antibodies are those which have agonistic or antagonistic IL-15 properties.

The present invention also relates to IL-15 muteins and IL-15 mutein fragments, which are derivable from the epitopic peptides of the invention.

The present application thus relates to IL-15 muteins, which comprise a sequence that is derivable from human mature wild-type IL-15 by at least one substitution, deletion or addition within the region spanning from residue 44 to residue 52, and/or from residue 64 to residue 68 and/or from residue 64 to residue 69 (all end point residues of said regions being explicitly included), this residue numbering corresponding to (and being maintained as that of) the human mature wild-type IL-15.

Preferably, the mutation(s) is(are) affinity-conservative or affinity-enhancing, such that the IL-15 mutein resulting therefrom has an affinity for binding to IL-15Ralpha that is either not significantly different from, or higher than the affinity of human mature wild-type IL-15 for binding to IL-15Ralpha.

When starting from human mature wild-type IL-15, residue E46 and I50 should preferably not be mutated as they tend to induce a reduction in affinity for IL-15Ralpha.

Equivalent muteins can be derived from other mature wild-type IL-15, such as notably non-human but animal mature wild-type IL-15, and more particularly non-human but mammal mature wild-type IL-15, e.g. simian, mouse, rat, bovine, sheep, pig or dog IL-15.

Said substitution can e.g. be a replacement of at least one hydrophobic side chain selected from L, V and I, and/or of at least one non-charged polar side chain selected from S, Q and N by a charged group selected from D, E, R and K, and/or a replacement of at least one charged polar side chain selected from E by an oppositely charged group selected from K and R.

The present invention further provides with IL-15 muteins that are IL-15 agonists or super-agonists.

Preferred agonistic muteins comprise a sequence that is derivable from human mature wild-type IL-15 by substitution of at least one of residues 45, 51, 52.

In human mature wild-type IL-15, residue 45 is L, residue 51 is S and residue 52 is L (see SEQ ID NO:2 on FIG. 1A).

The present invention particularly provides with IL-15 muteins that comprise a sequence that is derivable from human mature wild-type IL-15 by replacement of residue 45 by D, E K or R, preferably by D or E. They notably include the IL-15 muteins which comprise a sequence that is derivable from human mature wild-type IL-15 by substitution of the region spanning from residue 44 to residue 52 by the sequence of SEQ ID NO:7 or SEQ ID NO:8 or SEQ ID NO:9 or SEQ ID NO:10, e.g. the IL-15 muteins of sequence SEQ ID NO:29 or SEQ ID NO:30 or SEQ ID NO:31 or SEQ ID NO:32, respectively (see FIG. 2C). Most preferred agonistic muteins include those muteins which comprise the sequence of SEQ ID NO:29 or SEQ ID NO:30 (see FIG. 2C).

Other preferred IL-15 agonistic muteins include those muteins that comprise a sequence that is derivable from human mature wild-type IL-15 by replacement of residue 51 by D, E K or R, preferably by D. They notably include the IL-15 muteins which comprise a sequence that is derivable from human mature wild-type IL-15 by substitution of the region spanning from residue 44 to residue 52 by the sequence of SEQ ID NO: 11 or SEQ ID NO:12 or SEQ ID NO:13 or SEQ ID NO:14, e.g. the IL-15 muteins of sequence SEQ ID NO:33 or SEQ ID NO:34 or SEQ ID NO:35 or SEQ ID NO:36, respectively (see FIG. 2C). Most preferred agonistic muteins include those which comprise the sequence of SEQ ID NO:33 (see FIG. 2C).

Still other preferred IL-15 agonistic muteins include those muteins which comprise a sequence that is derivable from human mature wild-type IL-15 by replacement of residue 52 by D, E, K or R, preferably by D. They notably include the IL-15 muteins which comprise a sequence that is derivable from human mature wild-type IL-15 by substitution of the region spanning from residue 44 to residue 52 by the sequence of SEQ ID NO:15 or SEQ ID NO:16 or SEQ ID NO:17 or SEQ ID NO:18, e.g. the IL-15 muteins of sequence SEQ ID NO:37 or SEQ ID NO:38 or SEQ ID NO:39 or SEQ ID NO:40, respectively (see FIG. 2C). Most preferred agonistic muteins include those which comprise the sequence of SEQ ID NO:37 (see FIG. 2C).

Site-directed mutagenesis of peptide 1 shows that L45, E46, V49, S51 and L52 are involved in IL-15Ralpha binding, and that E46 is crucial, since replacement of its acidic side chain by a basic one (E46K) results in a complete loss of IL-15 binding to IL-15Ralpha and bio-activity. Mutation at position I50 (I50D) strongly reduced the ability of IL-15 to bind to IL-15Ralpha as well as to induce cell proliferation. Replacement of the hydrophobic side chain of V49 by a negatively charged side chain (V49D) also results in a strong (13 fold) reduction of the affinity of IL-15 for IL-15Ralpha.

Mutations at residue 46 or 49 or 50, such as E46K or V49D or I50D, thus tend to induce a significant loss in binding affinity. They are therefore generally not satisfactory, at least when introduced as a single-point mutation.

The present invention further provides with IL-15 muteins that are IL-15 antagonists or antagonist candidates.

Preferred antagonistic muteins comprise a sequence that is derivable from human mature wild-type IL-15 by substitution of at least one of residues 64, 65, 68, 69.

In human mature wild-type IL-15, residue 64 is E, residue 65 is N, residue 68 is I, residue 69 is L (see SEQ ID NO:2 on FIG. 1A).

Preferred IL-15 antagonistic muteins include those muteins which comprise a sequence that is derivable from human mature wild-type IL-15 by replacement of residue 64 by K or R. They notably include the IL-15 muteins which comprise a sequence that is derivable from human mature wild-type IL-15 by substitution of the region spanning from residue 64 to residue 68 by the sequence of SEQ ID NO:19 or SEQ ID NO:20, e.g. the IL-15 mutein of sequence SEQ ID NO:41 or SEQ ID NO:42 (see FIG. 2D). Most preferred antagonistic muteins include those which comprise the sequence of SEQ ID NO:41 (see FIG. 2D).

Other preferred IL-15 antagonistic muteins include those muteins which comprise a sequence that is derivable from human mature wild-type IL-15 by replacement of residue 65 by D, E, K or R, preferably by K. They notably include the IL-15 muteins which comprise a sequence that is derivable from human mature wild-type IL-15 by substitution of the region spanning from residue 64 to residue 68 by the sequence of SEQ ID NO:21 or SEQ ID NO:22 or SEQ ID NO:23 or SEQ ID NO:24, e.g. the IL-15 mutein of sequence SEQ ID NO:43 or SEQ ID NO:44 or SEQ ID NO:45 or SEQ ID NO:46, respectively (see FIG. 2D). Most preferred IL-15 antagonistic muteins include those which comprise the sequence of SEQ ID NO:43 (see FIG. 2D).

Still other preferred IL-15 antagonistic muteins include those muteins which comprise a sequence that is derivable from human mature wild-type IL-15 by replacement of residue 68 by D, E, K or R, preferably by K. They notably include the IL-15 muteins which comprise a sequence that is derivable from human mature wild-type IL-15 by substitution of the region spanning from residue 64 to residue 68 by the sequence of SEQ ID NO:25 or SEQ ID NO:26 or SEQ ID NO:27 or SEQ ID NO:28, e.g. the IL-15 mutein of sequence SEQ ID NO:47 or SEQ ID NO:48 or SEQ ID NO:49 or SEQ ID NO:50, respectively (see FIG. 2D). Most preferred IL-15 antagonistic muteins include those which comprise the sequence of SEQ ID NO:47 (see FIG. 2D).

Still other preferred IL-15 antagonistic muteins include those muteins which comprise a sequence that is derivable from human mature wild-type IL-15 by replacement of residue 69 by D, E, K or R, preferably by R. They notably include the IL-15 muteins which comprise a sequence that is derivable from human mature wild-type IL-15 by substitution of the region spanning from residue 64 to residue 69 by the sequence of SEQ ID NO:77 or SEQ ID NO:78 or SEQ ID NO:79 or SEQ ID NO:80 (see FIG. 9), e.g. the IL-15 mutein of sequence SEQ ID NO:82 or SEQ ID NO:83 or SEQ ID NO:84 or SEQ ID NO:85, respectively (see FIG. 10).

The present application also relates to the nucleic acids (DNA or RNA) coding for the IL-15 muteins of the invention, optionally contained within a vector, such as transfection vector, an expression vector.

The DNA encoding an IL-15 mutein may then be operably linked to a suitable transcriptional or translational regulatory sequence such as transcriptional promoters or enhancers, an optional operator sequence to control transcription, a sequence encoding suitable mRNA ribosomal binding sites, and appropriate sequences that control transcription and translation initiation and termination. Examples of such vectors include pEF1/myc-His (In Vitrogen, V921-20), pcDNA3.1 (In Vitrogen, V800-20).

It may also be linked to a leader sequence that enables improved extracellular secretion of the translated polypeptide. Examples of such leader sequences include Kozak and leader sequences from rat pre-prolactin (NCBI accession number AF022935, nucleotides 178 to 270; National Center for Biotechnology Information, U.S. National library of Medicine, 8600 Rockville Pike, Bethesda, Md. 20894, U.S.A.).

The recombinant expression vectors carrying the recombinant IL-15 mutein structural coding sequence may then be transfected or transformed into a host cell.

Suitable host cells for expression of an IL-15 mutein include prokaryotes, yeast or higher eukaryotic cells under the control of appropriate promoters. Prokaryotes include for example *Escherichia coli, Bacillus subtilis, Salmonella typhimurium*, and various other species within the genera *Pseudomonas, Streptomyces* and *Staphylococcus*. Examples of suitable host cells also include yeast such as *Saccharomyces cerevisiae*, a mammalian cell line such as Chinese Hamster Ovary (CHO) cells, e.g. Chinese ovary hamster cell line CHO/dhfr$^-$ (CHO duk$^-$) (ATCC no CRL-9096), or such as epithelial cell lines, e.g. simian epithelial cell line COS-7 (ATCC no CRL 1651), or human cell lines, e.g. 293 c18 human kidney cell line (ATCC no CRL-10852) or FreeStyle 293-F human kidney cell line (In Vitrogen no R790-07).

Appropriate cloning and expression vectors for use with bacterial, insect, yeast and mammalian cellular host are described for example, in Pouwels et al. *Cloning Vectors: A laboratory Manual*, Elsevier, N.Y. 1985.

The present application also relates to the conservative fragment of the IL-15 mutein of the invention. Such conservative IL-15 mutein fragments still comprise the mutated 44-52 region and/or mutated 64-68 region and/or mutated 64-69 region, and has retained an affinity for binding to IL-15Ralpha that is either not significantly different from, or higher than the affinity of human mature wild-type IL-15 for binding to IL-15Ralpha.

The present application more particularly relates to IL-15 mutein fragments which are IL-15 agonists, such as a fragment comprising the sequence of any one of SEQ ID NO:7-18, for example the peptide of SEQ ID NO:7 (L45D), or SEQ ID NO:8 (L45E), or SEQ ID NO:11 (S51D), or SEQ ID NO:15 (L52D); see FIG. 2A.

Figure 8:
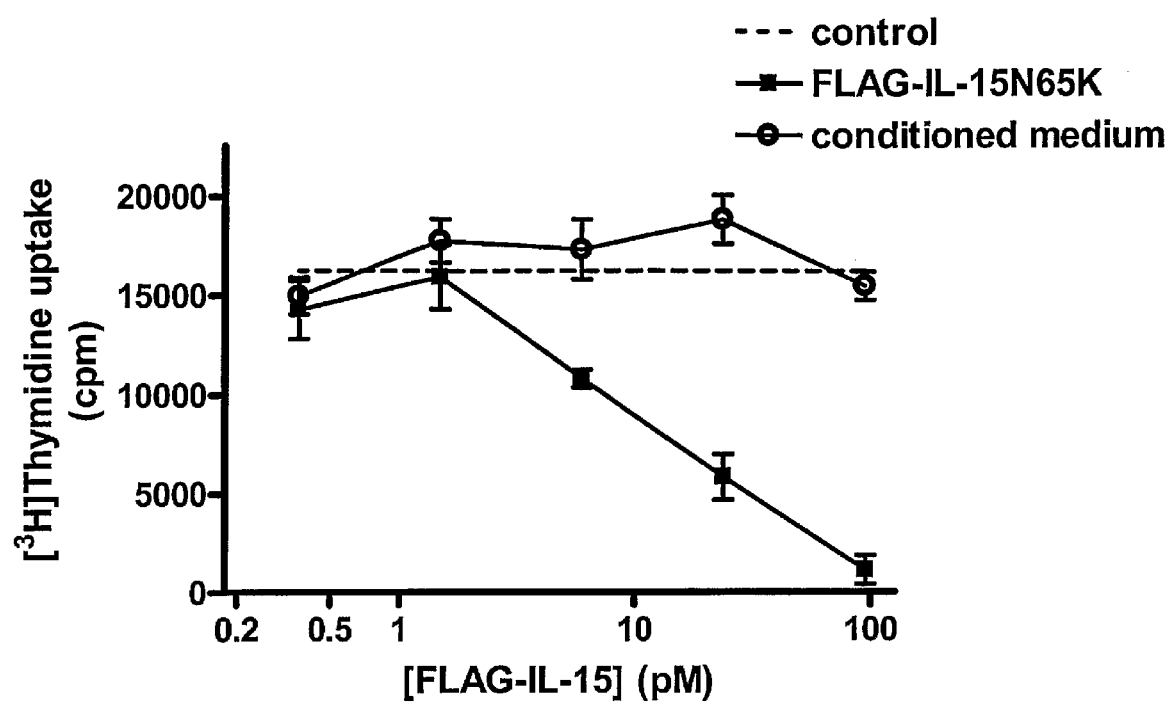
FIG. 8 illustrates the effect of N65K Flag-Il-15 mutant on IL-15 induced proliferation of TF-1β cells in presence of A41. Cell proliferation was evaluated by measuring the incorporation of [3H]thymidine. Cells were cultured in presence of 66 nM anti IL-2Rβ A41 mAb, with a fixed concentration of 10 pM r-IL-15 (control) and increasing concentrations of affinity purified Flag-IL-15N65K. A negative control was prepared by the affinity purification of conditioned medium from non-transfected 293-EBNA cells and introduced in the biological assay at the same dilutions as Flag-IL-15N65K.

The present application more particularly relates to IL-15 mutein fragments which are IL-15 antagonists or partial agonists or antagonist candidates, such as a fragment comprising the sequence of any one of SEQ ID NO:19-28, 77-80 (see FIGS. 2B and 9). For example the peptides of SEQ ID NO:19 (E64K), SEQ ID NO:25 (I68D) or SEQ ID NO:80 (L69R) behave as partial agonists; SEQ ID NO:80 (L69R) induces a maximal response that is as low as 2% of wild-type IL-15 activity. The peptide of SEQ ID NO:23 (N65K) behave as an antagonist (total inhibition of IL-15 activity at 100 pM of N65K mutein; see example 2 below and FIG. 8).

Similarly to what has been above described for the muteins of the invention, the present application also encompasses within its scope the nucleic acid (DNA or RNA) coding for the IL-15 mutein fragments of the invention, optionally contained within a vector; as well as any such vector, and any host cell containing such a nucleic acid.

The epitopic peptides and muteins of the invention can be produced by any means that the skilled person may find appropriate, such as e.g. chemical peptide synthesis, or peptide biosynthesis.

Chemical peptide synthesis is now a routine (see e.g. Andersson et al., 2000, Biopolymers (Peptide Science) 55: 227-250), and many companies are specialized in such synthesis. Preferably, the epitopic peptide and mutein fragments of the present invention are synthesized by solid phase peptide synthesis (SPPS) techniques using standard FMOC protocols (See, e.g., Carpino et al., 1970, J. Am. Chem. Soc. 92(19):5748-5749; Carpino et al., 1972, J. Org. Chem. 37(22):3404-3409).

Alternatively, the skilled person may choose to produce the muteins or mutein fragment biologically by in vitro or in vivo translation of a mutated expression cassette obtained from wild-type IL-15 by site-directed mutagenesis (Sodoyer, 2004, Biodrugs, 18 (1): 51-62).

An illustration thereof is described in the example below.

Amino-acid switching may then be performed by any mutagenesis means available to the skilled person, e.g. by using the QuikChange Site-Directed Mutagenesis Kit (Stratagene, La Jolla, Calif., U.S.A.). The mutated expression cassette can then be transfected host cells such as 293 c18 cells (ATCC no 10852) (Invitrogen, Leek, The Netherlands). Transfected cells may then be cultured so as to express the mutated cassette (293 c18 cells can e.g. be cultured in a DMEM containing 10% FCS, 2 mM glutamine, 1 mg/mL glucose, and 250 microgrammes/mL geneticin). The mutated expression product can then be recovered and optionally purified (e.g. collection of culture supernatants and purification thereof).

A process for the production of an IL-15 mutein or of an IL-15 mutein fragment according to the invention e.g. comprises:
  providing a nucleic acid according to the invention, which codes for said mutein or mutein fragment, said nucleic acid being optionally within a expression vector,
  operably introducing said nucleic acid into a host cell so that it produces the expression product thereof,
  recovering said expression product.

The IL-15 mutein may be concentrated using a commercially available protein concentration filter, such as an Amicon or Millipore Pellicon ultrafiltration unit.

The resulting expressed optionally concentrated mutein may then be purified from culture media or extracts. The culture media or cell extract may be applied to a purification matrix such as a hydrophobic chromatography medium, or an anion exchange resin. Concentration may then be further increased by RP-HPLC.

The concentrated mutein can also be purified through its N-terminal FLAG tag on an immuno-affinity column grafted with the anti-FLAG antibody M2 (Sigma product no A 2220).

Other tags (e.g. polyHistine tag) can be added by genetic engineering to the N or C terminal ends of the muteins in order to help its purification process.

The present application also relates to the biological and medical applications of the epitopic peptides, the IL-15 muteins, and the IL-15 mutein fragments of the invention, either in their aminoacid expression, or in their nucleic acid coding version.

The agonistic muteins of the invention are useful to expand lymphocyte subsets, such as particular T/NK subsets. The present invention thus relates to their use as an agent for expanding one or several lymphocyte populations, such as NK cells, NK-T cells, CD8+ memory cells, and to a composition or kit intended for such a use which comprises such an agonistic mutein.

The present invention particularly relates to a drug or vaccine, comprising an IL-15 mutein or IL-15 mutein fragment of the invention, and optionally a pharmaceutically acceptable vehicle and/or carrier and/or diluent and/or adjuvant.

Such a drug or vaccine is intended for prevention and/or treatment and/or alleviation of a condition or disease in which a reduction or increase of IL-15 activity is desired.

A number of studies have contributed to the identification of disorders in which targeting the IL-15 system is of clinical relevance and potential benefit. Among them are autoimmune and inflammatory diseases, infectious diseases, transplant rejection, cancer and immunodeficiencies (see bibliographic references 22, 23).

The present application particularly relates to a drug or vaccine comprising an IL-15 mutein or IL-15 mutein fragment of the invention, which is an IL-15 agonist of the invention, and optionally a pharmaceutically acceptable vehicle and/or carrier and/or diluent and/or adjuvant.

Such a drug or vaccine is intended for prevention and/or treatment and/or alleviation of a condition or disease in which an increase of IL-15 activity is desired, such as notably cancer or immunodeficiency. Such a drug or vaccine may act by stimulating the proliferation and/or survival of lymphocytes (such as T cells, CD8+ T cells, NK cells, dendritic cells) and/or their activity against tumoral cells.

The present application particularly relates to such a drug comprising an IL-15 mutein or IL-15 mutein fragment of the invention, which is an IL-15 antagonist of the invention, and optionally a pharmaceutically acceptable vehicle and/or carrier and/or diluent and/or adjuvant.

Such a drug is intended for prevention and/or treatment and/or alleviation of a condition or disease in which a reduction of IL-15 activity is desired, such as inflammatory diseases like rheumatoid arthritis and generalized Shwartzman reaction.

The present application further relates to a process for screening for an IL-15 agonist or antagonist, which comprises:
i. providing a plurality of IL-15 muteins, and/or of IL-15 mutein fragments according to the invention,
ii. comparing their respective binding affinity for IL15-Ralpha to the binding affinity of mature wild-type IL-15,
iii. selecting those muteins or mutein fragments which have a binding affinity that is not significantly different from, or that is higher than the one of mature wild-type IL-15.

To screen for an IL-15 agonist, the process may further comprises:
iv. selecting at least one detectable IL15-inducible activity,
v. comparing the level of said activity that is induced in response to the muteins or fragments selected in step iii., to the one induced by mature wild-type IL-15,
vi. selecting those muteins or fragments which induce an activity level that is not significantly different from, or that is higher than the one of mature wild-type IL-15.

To screen for an IL-15 antagonist, characterized in that it further comprises:
iv. selecting at least one detectable IL 15-inducible activity,
v. comparing the level of said activity that is induced in response to the muteins or fragments selected in step iii., to the one induced by mature wild-type IL-15,
vi. selecting those muteins or fragments which induce an activity level that is lower than the one of mature wild-type IL-15, or which induce no detectable level of activity.

The present invention is illustrated by the examples below. They are meant for illustrative purposes only, and do not limit the scope of the present invention.

EXAMPLE 1

Experimental Procedures

Cytokines and Antibodies

Recombinant murine IL-3 and human GM-CSF were purchased from R&D Systems (Abington, UK), recombinant human IL-15 (rIL-15) was purchased from Peprotech Inc (Rocky Hill, N.J.), and recombinant human IL-2 (rIL-2) from Chiron (Emeryville, Calif.). Polyclonal goat anti-human IL-2 AF-202-NA was purchased from R&D Systems and the mouse anti-human IL-2 mAb IL2.66 was from Immunotech (Marseille, France). Monoclonal mouse anti-human IL-15Rα M161 was kindly provided by GenMab A/S (Copenhagen, Denmark) [for the below-described experiments, polyclonal antibody AF247 (R&D Systems Inc., Minneapolis, USA) can alternatively be used], and mouse anti-FLAG mAb M2 conjugated to peroxidase was purchased from Sigma (Saint Quentin Fallavier, France).

Cell Culture

The non-adherent TF-1 human cell line is available from the American Type Culture Collection (ATCC; 10801 University Blvd.; Manassas, Va. 20110-2209; U.S.A.), and has ATCC accession number CRL-2003. TF-1β human cells are available by operably transfecting TF-1 cells with beta chains so that the TF-1β cells resulting therefrom proliferate in response to IL-15 (see bibliographic reference 29).

Beta chain templates are available from RNA of HuT102 (ATCC TIB-162) or Jurkat clone E6.1 (ATCC TIB 152) by RT-PCR using the proofreading polymerase Pfu (Stratagène no 600390) and 5'GAGAGACTGGATGGACCC 3' as sense primer (SEQ ID NO:51), and 5' AAGAAACTAACTCT-TAAAGAGGC3' as anti-sense primer (SEQ ID NO:52) according efficiently cloned using the Zero Blunt PCR Cloning Kit (In Vitrogen cat no K2700-20) or the TOPO XL PCR cloning kit (In Vitrogen cat no K4750-10). The cDNA for IL-2R beta gene is then subcloned into the multiple cloning site of the pLXRN retrovirus expression vector of the Pantropic Retroviral Expression System (BD Biosciences Clontech no 631512) and transfected into GP2-293 cells, as described in the kit to generate recombinant retroviruses. IL-2R beta recombinant retroviruses can then be used to infect TF-1 cells to generate TF-1β after selection in medium containing G418.

The adherent CHO duk-cell line is available from the ATCC(CHO/dhfr-; accession number CRL-9096).

All cells were grown in 5% $CO_2$ at 37° C. in a water-saturated atmosphere. The non-adherent TF-1 human cell line, TF-1β human cells and adherent CHO duk-cell line were cultured in a RPMI 1640 medium containing 10% heat-inactivated fetal calf serum (FCS), 2 mM glutamine, and specific reactants as follow: 1 ng/ml of GM-CSF (TF1), 1 ng/ml GM-CSF and 250 µg/ml geneticin (TF-1β), 10 µg/ml of adenosine, deoxyadenosine, and thymidine (Dhfr⁻ CHO duk-). The non-adherent CTLL-2 murine cell line was cultured in a RPMI 1640 medium containing 8% FCS, 2 mM glutamine, 15 ng/ml rIL-2, and 50 µM 2-mercaptoethanol. Adherent 293 c18 human cells (Invitrogen, Leek, The Netherlands) were cultured in a DMEM containing 10% FCS, 2 mM glutamine, 1 mg/ml glucose, and 250 µg/ml geneticin.

Preparation of Soluble IL-15Rα-IL-2 Fusion Protein

Human IL-15Rα templates are available by RT-PCR from RNA of TF-1 cells (ATCC accession number CRL-2003) or of normal human monocytes purified from blood, using the proofreading polymerase Pfu (Stratagène no 600390) and 5' AGTCCAGCGGTGTCCTGTGG 3' as sense primer—SEQ ID NO:53—, and 5' TCATAGGTGGTGAGAGCAGT 3' as anti-sense primer—SEQ ID NO:54—according to human IL-15Rα sequence (NCBI accession number U31628). The PCR product is cloned using the Zero Blunt PCR Cloning Kit (In Vitrogen cat no K2700-20), to create a pNo15R plasmid.

Human IL-2 templates are available by RT-PCR from RNA of Jurkat cells clone E6-1 (ATCC accession number TIB-152) stimulated with OKT3 antibody and PMA (30), using the proofreading polymerase Pfu (Stratagène no 600390) and 5' AACTGCAGGCACCTACTTCAAGTTCTAC 3' as sense primer (Pst I underlined)—SEQ ID NO:55—, and 5' TCC CCCGGGTCAAGTCAGTGTTGAGATG 3' as anti-sense primer (Sma I underlined)—SEQ ID NO:56—according to human IL-2 sequence (NCBI accession number NM000586). The PCR product is cloned into the bluescript plasmid (NCBI accession number X52328) between Pst I and Sma I sites, to create a pBSSK-IL-2 plasmid.

To generate the chimeric soluble IL-15Rα-IL-2 construct, the signal peptide and the extracellular domain of IL-15Rα (nucleotides 1-697) were PCR amplified from pNoR15, using the sense primer—SEQ ID NO:57—5'-GGG AAGCTTAGTCCAGCGGTGTCCTGT-3' (primer 1, nested Hind III restriction site underlined) and the antisense primer—SEQ ID NO:58—5'-AA CTGCAGAGTGGTGTCGCTGTGGCC-3' (primer 2, Pst I underlined). The amplified product was then cloned between the Hind III and Pst I sites of pBSSK-IL-2.

In the final hybrid gene, the Pst I site (coding for the dipeptide Leu-Gln) behaved as a linker between the IL-15Rα (5' end) and IL-2 (3' end) sequences. The sequence was controlled and the chimeric construct was digested from the bluescript plasmid between the Hind III/Not I sites and subcloned into the mammalian expression vector pKCR6 (31) at the Eco RI site. Dhfr-CHO cells were transfected with pKCR6-sIL-15Rα-IL-2 using SuperFect Reagent (Qiagen, Courtaboeuf, France). Clones producing the fusion protein were detected using an ELISA for detection of human IL-2 (BioSource, Nivelles, Belgium). Three rounds of cloning were performed using increasing concentrations of methotrexate (Sigma). One clone selected at 5 µM methotrexate produced about 4.3 mg/l of sIL-15Rα-IL-2. The supernatants were concentrated by precipitation with ammonium sulfate at 60% saturation, loaded onto an IL-2 immunoaffinity column (mAb IL2.66), and the IL-2 fusion protein was purified as described (32). Its concentration was determined in the ELISA for human IL-2. Its purity was at least 80% with a molecular mass of 60 kDa, as assessed by SDS-PAGE after iodination with a chloramine T method as described previously (12). Full functionality of the IL-2 portion of the fusion protein was demonstrated in a CTLL-2 proliferation assay (cell proliferation kit II, Roche Diagnostics, Mannheim, Germany), using rIL-2 as standard. High affinity IL-15 binding of the IL-15Rα portion was demonstrated using the surface plasmon resonance technology (Biacore AB, Uppsala, Sweden).

Production of IL-15 Mutants

The pEF-neo PPL SP-IL-15 (human) expression construct was built in the pEF-1/myc-His vector (In Vitrogen, ref V921-20). The rat preprolactin signal peptide (PPL SP) sequence was amplified by RT-PCR of mRNA prepared from GH4C1 cells (ATCC accession number CCL-82.2) using 5' GG GGTACCATCACCATGAACAGCCAAG 3' as sense primer (Kpn I site underlined)—SEQ ID NO:59—and 5' CG GGATCCGGTCTGCACATTTTGGCAG 3' as anti-sense primer (Bam: H1 site underlined)—SEQ ID NO:60—, according to *rattus norvegicus* preprolactin sequence (NCBI accession number AF022935). The mature human IL-15 coding sequence was amplified by RT-PCR of mRNA from normal human keratinocytes prepared from foreskin obtained after circumcision, using 5' CG GGATCCAACTGGGTGAATGTAATAAG 3' as sense primer (Bam H1 site underlined)—SEQ ID NO:61—and 5' G GAATTCTCAAGAAGTGTTGATGAAC 3' as anti-sense primer (Eco R1 site underlined)—SEQ ID NO:62—, according to human IL-15 sequence (NCBI accession number N4000585). The PPL SP was introduced between the Kpn I and Bam H1 sites of pEF-1/myc-His, and IL-15 between the Bam H1 and Eco R1 sites of pEF-1/myc-His.

The FLAG tag (DYKDDDDK; SEQ ID NO:63) was introduced at the BamH1 site between the PPL SP and the mature IL-15 protein coding sequence as a double stranded oligonucleotide (SEQ ID NO:64=5'-GATCGGACTACAAGGAT-GACGATGACAAGC-3' and SEQ ID NO:65=5'-GATCGCTTGTCATCGTCATCCTTGTAGTCC-3'). A bluescript plasmid containing the PPL-FLAG-IL-15 sequence was generated by subcloning the Kpn I/Eco R1 fragment. Amino-acid switching was performed using the QuikChange Site-Directed Mutagenesis Kit (Stratagene, La Jolla, Calif.) with the bluescript construct. Sequences were confirmed over the PPL-FLAG-IL-15 hybrid cDNA and the mutated Kpn I/Eco R1 fragment was cloned back into pEF-1/myc-His. For the production of a FLAG-IL-15 mutant, $3.2 \times 10^6$ adherent 293 c18 cells were transfected with 16 µg of the mutated IL-15 expression construct in a 60 mm plate following a standard calcium phosphate protocol. After 6 h, the medium was replaced with fresh complete DMEM (Life Technologies, Cergy Pontoise, France) and supernatants were harvested 48 h after transfection.

Pepscan Analysis

The overlapping synthetic peptides were synthesized and screened using credit-card format mini-PEPSCAN cards (455 peptide format/card) as described previously (33). The 455-well credit-card format polyethylene cards, containing the covalently linked peptides, were incubated at 4° C. overnight with the samples (soluble IL-15Rα-IL-2 fusion protein) diluted in blocking solution containing 5% horse-serum (v/v) and 5% ovalbumin (w/v). After washing, the cards were incubated (1 h, 25° C.) with the anti-human IL-2 antibody AF-202-NA (1 µg/ml), washed and further incubated with peroxidase-coupled rabbit anti-goat IgGs at 1.3 µg/ml (P 0160, DakoCytomation). After washing, the peroxidase substrate 2,2'-azino-di-3-ethylbenzthiazoline sulfonate (ABTS) plus 2 µl/ml 3% $H_2O_2$ were added, and the color development was quantified at 1 h, using a CCD-camera and an image processing system. The setup consists of a CCD-camera and a 55 mm lens (Sony CCD Video Camara XC-77RR, Nikon micro-nikkor 55 mm f/2.8 lens), a camera adaptor (Sony Camara adaptor DC-77RR) and the Image Processing Software package Optimas, version 6.5 (Media Cybernetics, Silver Spring, Md.), run on a Pentium II computer system. The CCD-camera is equipped with an orange filter that translates the green color of the ABTS substrate into grey values (arbitrary scale).

IL-15 Binding Assays

Human rIL-15 was radio-labeled with $[^{125}I]$-iodine (specific radioactivity of around 2000 cpm/fmol) using a chloramine T method (34), and binding experiments were performed as described previously (12). Non specific binding was determined in the presence of 100 fold excess of unlabeled cytokine. For the IL-15 binding experiments, TF-1 cells were incubated with increasing concentrations of labeled rIL-15. Regression analysis of the binding data was accomplished using a one-site equilibrium binding equation (Grafit, Erithacus Software, Staines, UK) and data was plotted in the Scatchard coordinate system. For inhibition of IL-15 binding experiments, TF-1 cells were incubated with a fixed concentration of iodinated rIL-15 and increasing concentrations of FLAG-IL-15 or mutants or mAbs. Regression analysis of data was accomplished using a 4 parameter logistic equation (Grafit, Erithacus Software).

Proliferation Assays

The proliferative inducing activity of FLAG-IL-15 and mutants and the inhibitory activity of mAbs were assessed by [³H]-thymidine incorporation on TF-1β cells. Cells were maintained in the culture medium for 3 days, washed twice, and starved for 2 h in the same medium without cytokine. They were plated at $10^4$ cells in 100 µl and cultured for 48 h in the medium supplemented with increasing concentrations of rIL-15, FLAG-IL-15 or mutant, or in the medium supplemented with a fixed concentration of rIL-15 and increasing concentration of mAbs. Cells were pulsed for 16 h with 0.5 µCi/well of [³H]-thymidine, harvested onto glass fiber filters, and cell-associated radioactivity was measured.

Results

Analysis of IL-15Rα Binding to IL-15 by a Pepscan Approach

A pepscan approach was used in an attempt to identify IL-15 regions directly involved in IL-15Rα binding. For that purpose, a soluble fusion protein (sIL-15Rα-IL-2) consisting of the extracellular domain of human IL-15Rα fused to human IL-2 was assayed for binding to the 12-mer IL-15 peptides, using a polyclonal anti-human IL-2 antibody (AF-202-NA) as the revealing antibody (FIG. 3A). Two main peaks of reactivity were observed that corresponded to the binding of sIL-15Rα-IL-2 with two different regions of the IL-15 sequence. Control experiments with a similar concentration (330 mM) of rIL-2 gave background reactivity (FIG. 3A). Pepscan studies on 30-mer peptide of human IL-15 confirmed the reactivity of sIL-15Rα-IL-2 with these two IL-15 regions. Analysis of the 2 sets of peptides (12-mer and 30-mer) associated with the reactivity allowed to assign the following sequences as responsible for sIL-15Rα-IL-2 binding: $_{44}$LLELQVISL$_{52}$ (peptide 1; SEQ ID NO:4) and $_{64}$ENLII$_{68}$ (peptide 2; SEQ ID NO:6). The first sequence is located within helix B, and the second sequence in helix C (FIG. 3B).

IL-15 Site-Directed Mutagenesis

Figure 4A:
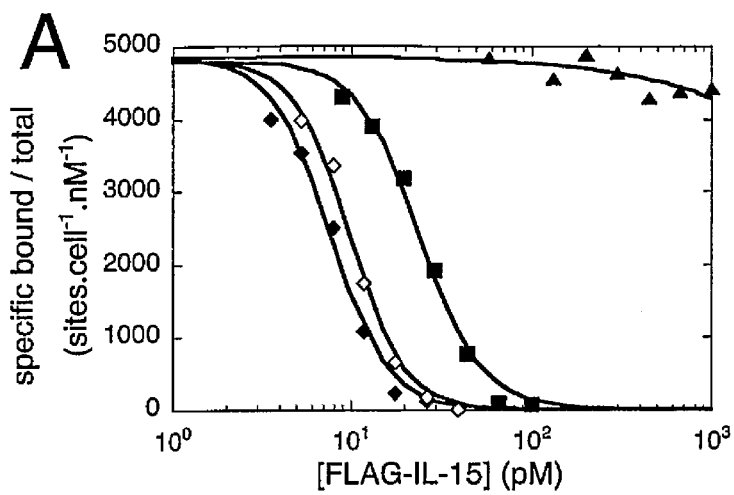
FIGS. 4A, 4B and 4C illustrate the determination of the affinities of FLAG-IL-15 and mutants for IL-15Rα by competition binding studies: TF-1 cells were equilibrated with a fixed concentration (80 pM) of [$^{125}$I]-rIL-15 and increasing concentrations (as indicated on the abscissa) of the FLAG-IL-15 wild type (WT) or mutants.
Figure 4B:
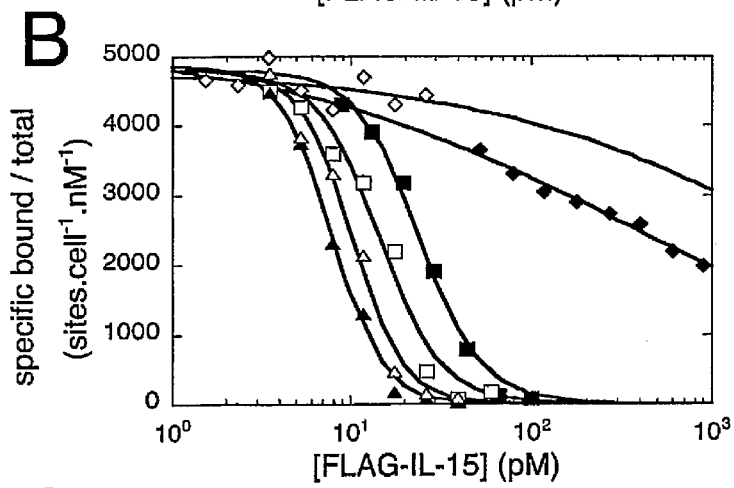
Figure 4C:
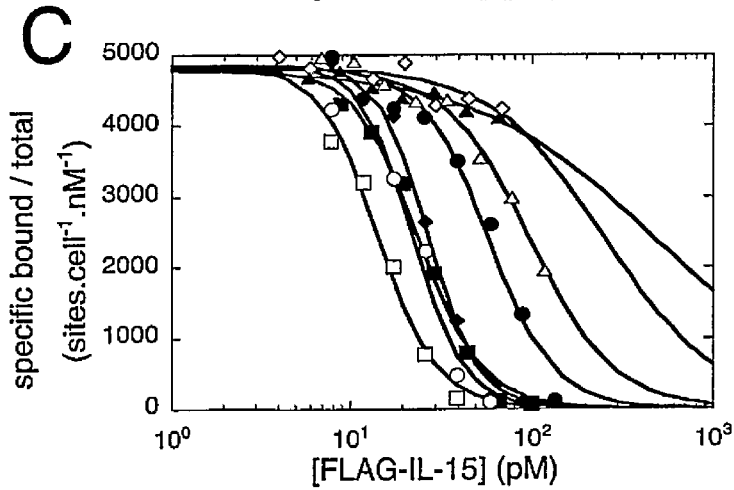

In order to confirm the involvement of the two peptidic regions identified by pepscan in the binding to the IL-15R chain, point mutations of IL-15 in these regions were carried out. In order to introduce a substantial disturbance in the presumed receptor binding site, non-polar hydrophobic side chains (L, V, I) and non-charged polar side chains (S, N, Q) were replaced by charged groups (D, E or K), and charged polar side chains (E) were replaced by oppositely charged groups (K). Mutants were generated at positions 44 to 52 (peptide 1) and positions 64 to 68 (peptide 2). Wild-type human IL-15 and mutants were expressed as fusion proteins with a N-terminal FLAG peptide in the 293 c18 cells. FLAG-IL-15 and mutants were then assayed for their ability to bind IL-15Rα expressed by TF-1 cells (FIGS. 4A, 4B, 4C). For that purpose, a competition assay was used that allowed to compare the efficiencies of the different mutants to inhibit the binding of a low, non-saturating concentration of radio-iodinated rIL-15 to TF-1 cells. The competition curves are shown in FIG. 4A, 4B, 4C and the concentrations of mutants giving half maximal inhibitory effects (IC50s) are listed in Table I.

TABLE I

TABLE I Binding properties of the IL-15 mutants on the TF-1 cell line.

| FLAG-IL-15 Proteins | $IC_{50}$ (pM) | Relative activity (% WT) |
|---|---|---|
| W T | 26.1 | 100 |
| L44D | ND | NA |
| L45D | 10.1 | 258 ± 30 |
| L45E | 12.5 | 209 ± 10 |
| E46K | 13314.7 | 0.20 ± 0.01 |
| L47D | ND | NA |
| Q48K | 20.5 | 127 ± 27 |
| V49D | 347.7 | 8 ± 2 |
| I50D | 2949.8 | 0.88 ± 0.45 |
| S51D | 11.6 | 225 ± 36 |
| L52D | 10.9 | 239 ± 5 |
| E64K | 18.2 | 143 ± 43 |
| N65K | 26.6 | 98 ± 26 |

TABLE I-continued

TABLE I Binding properties of the IL-15 mutants on the TF-1 cell line.

| FLAG-IL-15 Proteins | IC$_{50}$ (pM) | Relative activity (% WT) |
|---|---|---|
| L66D | 190.9 | 14 ± 8 |
| L66E | 407.1 | 6 ± 2 |
| I67D | 104.8 | 25 ± 6 |
| I67E | 63.7 | 41 ± 9 |
| I68D | 20.2 | 129 ± 28 |

ND: not determined. NA: not applicable. Mean and standard deviations of the relative activities are from three independent experiments.

FLAG-IL-15 inhibited labeled rIL-15 binding with an IC50 of 26 pM.

Mutations at three positions (E46, V49 and I50) within peptide 1 had profound effects on the affinity of IL-15, whereas mutation Q48K was without effect. Mutations at position L45 (L45D and L45E), S51 and L52 reproducibly resulted in an increased (2 to 3 fold) affinity of IL-15 in this competition assay. The mutants L44D and L47D could not be evaluated in this assay because of too low production levels in 293 c18 supernatants. Some mutations in the peptide 2 region (those directed to residues L66 and I67) also strongly reduced the affinity of IL-15, whereas mutations at positions E64, N65 and I68 were without significant effects.

Figure 5A:
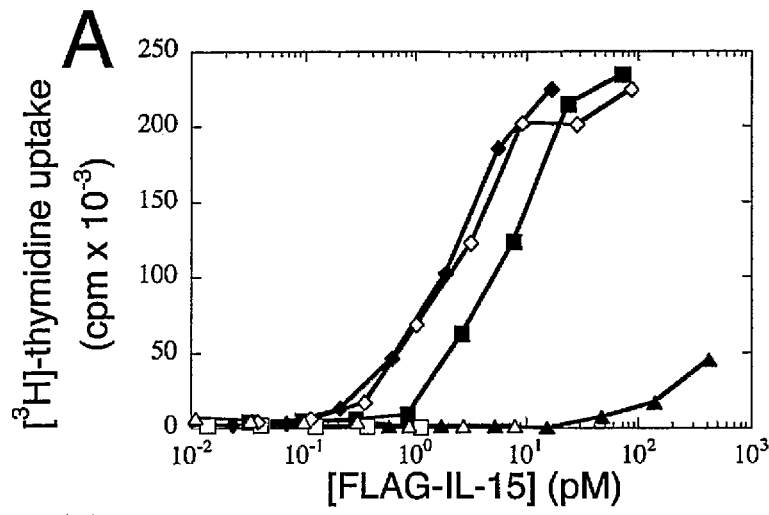
FIGS. 5A, 5B, 5C illustrate the proliferative activities of FLAG-IL-15 and mutants on TF-1β cells: TF-1β cells were cultured in the presence of increasing concentrations (as indicated on the abscissa) of FLAG-IL-15 wild type (WT) or mutants. Cell proliferation was evaluated by measuring the incorporation of [$^3$H]-thymidine.
Figure 5B:
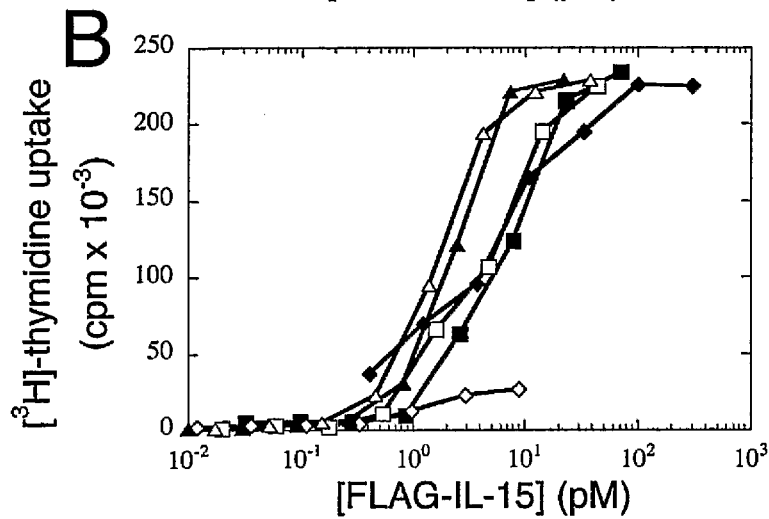
Figure 5C:
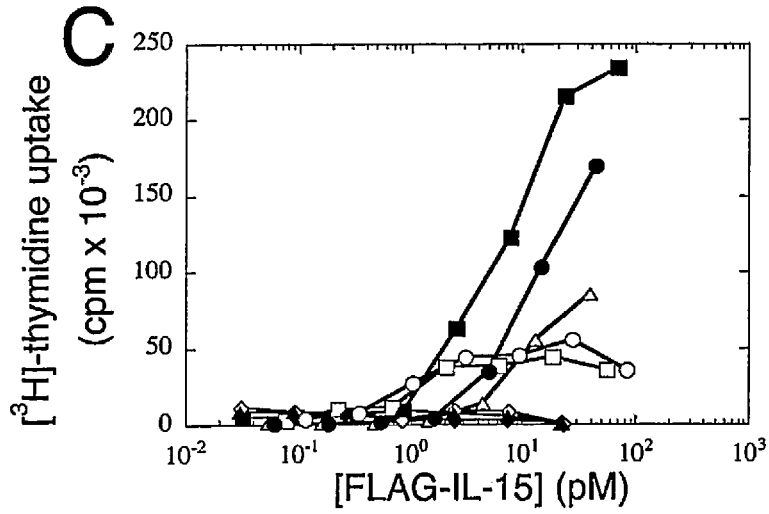

Wild-type FLAG-IL-15 and mutants were then tested for their growth-promoting effects on the IL-15 responsive TF-1β cells (FIGS. 5A, 5B, 5C and table II).

TABLE II

| FLAG-IL-15 proteins | Maximal induction (% WT) | EC$_{50}$ (pM) | Relative activity (% WT) |
|---|---|---|---|
| W T | 100 | 6.0 | 100 |
| L44D | 0 | >20.0 | <30 |
| L45D | 100 | 1.7 | 353 ± 73 |
| L45E | 100 | 2.4 | 250 ± 21 |
| E46K | >20 | >1300.0 | <0.5 |
| L47D | 0 | >60.0 | <10 |
| Q48K | 100 | 4.8 | 125 ± 22 |
| V49D | 100 | 6.2 | 97 ± 55 |
| I50D | >10 | >60.0 | <10 |
| S51D | 100 | 1.9 | 316 ± 26 |
| L52D | 100 | 1.7 | 353 ± 91 |
| E64K | 20 | ≈0.8 | NA |
| N65K | 0 | >200.0 | <0.4 |
| L66D | 0 | >200.0 | <0.4 |
| L66E | 0 | >200.0 | <0.4 |
| I67D | >40 | >30.0 | <3 |
| I67E | >75 | >10.0 | <8 |
| I68D | 20 | ≈0.8 | NA |

The peptide 1 mutants displayed biological activities that correlated well with their IL-15Rα binding efficiencies measured on TF-1 cells: the L44D, E46K, L47D, and I50D mutations resulted in a strong reduction of the biological activity of IL-15, whereas mutation Q48K was without significant effect, and mutations at positions L45, S51 and L52 induced a 2 to 4 fold increase in bioactivity. The only exception was mutant V49D which, despite a strongly reduced binding capacity, displayed nearly wild-type bioactivity. In contrast, the correlation between biological activity on TF-1β cells and binding affinity on TF-1 cells was far weaker with mutants in the peptide 2 region. Mutant N65K who displayed a nearly wild-type binding affinity on TF-1 cells was inactive on TF-1β cells. Mutant E64K and I68D who also displayed nearly wild-type binding affinities behaved as partial agonists on TF-1β with maximal responses being about 20% that of wild-type IL-15. The only correlation was found for mutations at the L66 and I67 positions. The mutants L66D, L66E, I67D and I67E displayed reduced bioactivity with a ranked order of potencies similar to that seen in the competition binding assay.

Discussion

As opposed to the IL-2Rα chain which binds IL-2 with low affinity (35), the IL-15Rα chain has been shown per se to display high affinity binding for IL-15 (11). The interface between IL-15 and IL-15Rα therefore likely contributes to most of the free energy of binding of IL-15 to its functional high affinity (αβγ) receptor. To design proteins with agonist or antagonist properties of the IL-15 system, a good knowledge of the molecular features of the IL-15/IL-15Rα interface is therefore desirable. No data are available so far on that topic and the main aim of this study was to contribute to the definition of the epitope in IL-15 responsible for the binding of IL-15Rα.

Two regions were first identified by pepscan that specifically bind a soluble form of IL-15Rα. The first one ($_{44}$LLELQVISL$_{52}$, peptide 1) is located in the B helix, while the second ($_{64}$ENLII$_{68}$, peptide 2) belongs to the C helix.

Mutagenesis studies confirmed the involvement of these two regions and enabled us to identify amino-acids that participate in receptor binding and induction of bio-activity. Mutation at that position (I50D) strongly reduced the ability of IL-15 to bind to IL-15Rα as well as to induce cell proliferation, a result that might reflect a local conformational change that affect binding and signaling. However, this conformational change seems to not disturb the overall structure of the molecule.

E46, V49, L45, S51 and L52 were found to be involved in IL-15Rα binding. E46 was crucial, since replacement of its acidic side chain by a basic one (E46K) resulted in a complete loss of IL-15 binding to IL-15Rα and bio-activity.

Replacement of the hydrophobic side chain of V49 by a negatively charged side chain (V49D) also resulted in a strong (13 fold) reduction of the affinity of IL-15 for IL-15Rα. Unexpectedly, the V49D mutant showed almost wild-type biological activity. A similar discrepancy between binding affinity and bio-activity has been reported for an IL-2 mutant (T51P) (36). This mutant was as active as wild-type IL-2, although it displayed a 10 fold lower receptor binding affinity. It has been shown that this mutant was deficient in inducing internalization of high-affinity receptors, thus resulting in longer duration of receptor occupancy and induction of biological response. Whether the V49D IL-15 analog exhibits similar properties needs to be checked.

Mutations at positions L45, S51 and L52 did not result in reduction but to an increase in binding and bio-activity, indicating that these residues are also involved in IL-15Rα binding. The mutants L44D and L47D showed impaired biological responses, although their binding affinity could not be evaluated. Unexpectedly, mutant Q48K showed almost wild-type properties, although Q48 is positioned in the center of an epitope formed by amino-acids (L45, E46, V49, S51 and L52) which participate in receptor binding. Additional mutations of that residue might be required to reassess its potential involvement in receptor binding.

The results of mutagenesis in the peptide 2 region showed that among the 5 amino-acids evaluated (E64 to I68), only L66 and I67 seem to be involved in receptor binding. The mutants (L66D, L66E, I67D and I67E) displayed reduced binding affinities and corresponding reductions of their biological activities. Mutants E64K and I68D had affinities similar to that of wild-type IL-15, suggesting that E64 and I68 are not involved in IL-15Rα binding. However, the mutants behaved as partial agonists in the proliferation assay. Since partial agonism is indicative of defective activation of the receptor (37), E64 and I68 might be involved in the recruitment of the IL-2Rβ/γ transduction complex. This conclusion might hold for N65 whose mutation (N65K) resulted in a loss of bio-activity without detectable alteration of the IL-15Rα binding affinity. Mutagenesis of mouse IL-2 and molecular modeling studies (27, 38) have indicated that, in addition to residue D20 located on helix A (24), the C helix of human IL-2 is also potentially involved in its interaction with IL-2Rβ, and recent work has shown that a mutation in that helix (N88R) resulted in a drastic (1000 fold) loss of IL-2 binding to IL-2Rβ (26). Our results suggest that the corresponding region in human IL-15, especially residues E64, N65 and I68, participate also in the recruitment of the IL-2Rβ chain.

The IL-15 mutants E64K, N65K and I68D display properties (low or no biological activity despite high affinity binding to IL-15Rα) that designate them as potential IL-15 antagonists. Preliminary experiments indeed indicate that N65K can inhibit IL-15 induced cell proliferation.

The region of IL-15 which corresponds to peptide 2 seems to participate both in IL-15Rα and IL-2Rβ binding. Mutagenesis revealed that all amino-acids of peptide 2 (E64 to I68) are involved in this process.

The involvement of the epitope corresponding to peptide 2 in both IL-15Rα binding and IL-2Rβ recruitment might have implications on the dynamics of the receptor assembly. IL-15 would first bind with high affinity to IL-15Rα by engaging the peptide 1 and peptide 2 (or part of it) epitopes. Subsequent IL-2Rβ recruitment could then involve the engagement of another part of the peptide 2 epitope. Alternatively, a conformational change could occur in which IL-2Rβ would replace IL-15Rα in binding to the peptide 2 epitope.

In the case of mouse IL-2, a sequence of helix B analogous to the epitope in IL-15 corresponding to peptide 1 has been shown to interact with IL-2Rα (namely residues E76, P79, V83 and L86) (27). In the case of human IL-2, no mutations in the B helix that affect IL-2 binding to IL-2Rα have been described so far, although molecular modeling has predicted a contact between helix B of human IL-2 (namely residues K64 and E68, or E61 and E62) and IL-2Rα (38). In contrast, the region in IL-2 within helix C analogous to the epitope in IL-15 corresponding to peptide 2 does not appear to be involved in IL-2Rα binding (27). Our results therefore indicate that the mode of interaction of IL-15 with IL-15Rα is not completely homologous to the mode of interaction of IL-2 with IL-2Rα. This may reflect the fact that IL-15 displays an affinity for its α chain that is about 500 fold higher than the affinity of IL-2 for its α chain.

In conclusion, we identified two regions in IL-15 that are involved in the binding to IL-15Rα, one of them being also used to recruit the IL-2Rβ transducing subunit. IL-15 muteins (L45D, L45E, S51D and L52D) which display binding and biological properties higher than those of wild-type IL-15 and therefore behave as super-agonists are valuable tools to expand lymphocyte subsets (e.g. NK cells, NK-T cells, $CD8^+$ memory T cells) and might be useful as therapeutic agents in patients with cancer or immunodeficiencies. Other muteins (E64K, N65K and I68D) display properties that designate them as potential IL-15 antagonists, and might be useful in inflammatory diseases like rheumatoid arthritis and generalized Shwartzman reaction where IL-15 is thought to play an important role (22).

EXAMPLE 2

Experimental Procedures

IL-15 Site-Directed Mutagenesis.

IL-15 site-directed mutagenesis was performed as described in example 1 (QuikChange site-directed mutagenesis kit).

Purification of Flag-IL-15 protein. Mutant Flag-IL-15 protein was affinity-purified. 100 ml of supernatant harvested from 48 h post-transfection cultures of 293-EBNA cells were precipitated with 70% saturating concentration of ammonium sulphate. 293-EBNA cells have the designation 293 c18, and are available from ATCC under accession number CRL-10852 (American Type Culture Collection ATCC; P.O. Box 1549; Manassas, Va. 20108; U.S.A.). The pellet was dissolved in TBS (50 mM Tris pH 7.4, 150 mM NaCl) and dialysed against TBS in 6-8000 Daltons cutoff Spectra/Por tubing. Dialysate was batch purified over 100 µl anti Flag M2 affinity gel (Sigma-Aldrich). Mutant Flag-IL-15 protein was eluted from the gel with 800 µl 100 mM glycine pH 3.5 and neutralized with 1M Tris pH 8. Purified protein was dialysed against RPMI and filter-sterilized before being tested in a proliferation assay.

Proliferation assays. The inhibitory activity of mutant Flag-IL-15 was assessed by [3H]thymidine incorporation on TF-1β cells (obtained as described in example 1 above) in presence of 66 r anti-IL-2Rβ A41 mAb [available from Roche Diagnostic GmbH (Penzberg, Germany); for these experiments, any anti-IL2Rβ antibody showing an inhibitory activity on IL2Rβ-mediated bioactivities can alternatively be used, such as e.g. polyclonal AF-224-NA (R&S Systems Inc., Minneapolis, USA].

Cells were maintained in the culture medium for 3 days, washed twice, and starved for 2 h in the same medium without cytokine. They were plated at $10^4$ cells in 100 µl and cultured for 48 h in the medium supplemented with 66 nM A41 mAb, 10 pM fixed concentration of rIL-15 and increasing concentration of mutant Flag-IL-15. Cells were pulsed for 16 h with 0.5 µCi/well of [3H]thymidine and harvested onto glass fiber filters, and cell-associated radioactivity was measured.

Results:

IL-15 Site-directed mutagenesis. Mutants were generated at positions 64-68 (peptide 2) and 64-69 (peptide 2a), and expressed as fusion proteins with an N-terminal FLAG peptide in 293-EBNA cells.

Figure 6:
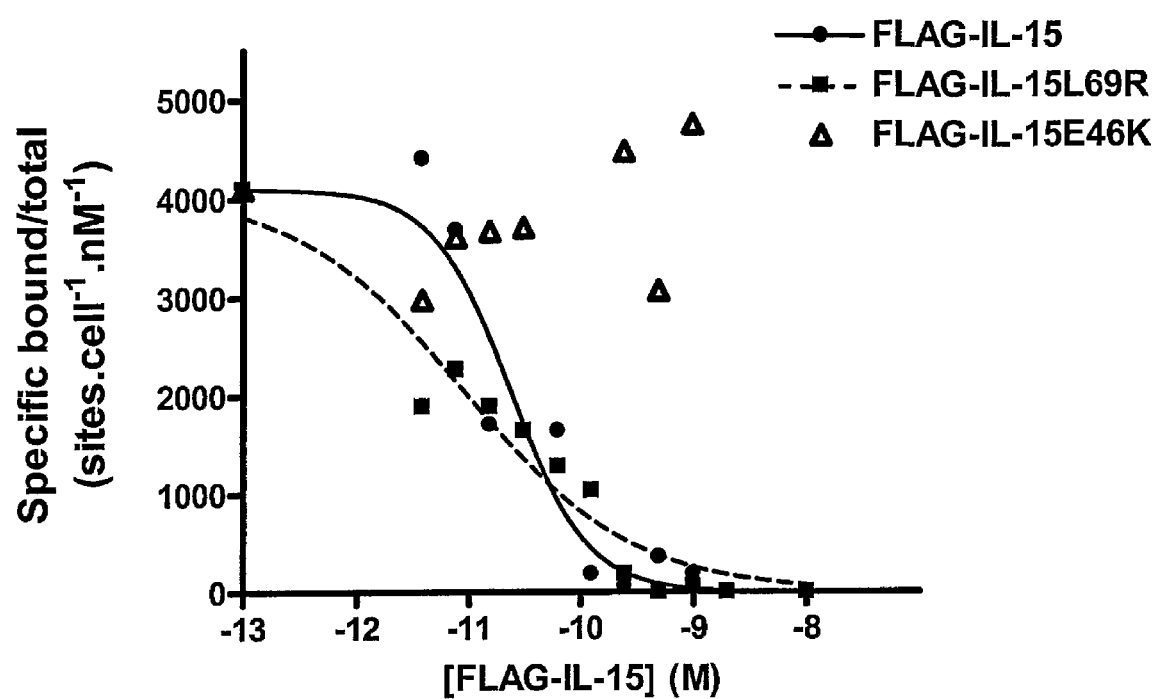
FIG. 6 illustrates the determination of the affinities of Flag-IL-15 and mutants for IL-15Rα by competition binding studies. TF1 cells were equilibrated with a fixed concentration (80 pM) of $^{125}$I-rIL-15 and increasing concentrations of the wild type Flag-IL-15 or mutant L69R and E46K. Specific rIL-15 cell binding was calculated and plotted as described in FIG. 4A.

FLAG-IL-15 mutants were assayed for their ability to bind IL-15Rα expressed by TF-1 cells in a competition assay that allowed us to compare the efficiencies of the different mutants to inhibit the binding of a low, non-saturating concentration of radioiodinated rIL-15 to TF-1 cells. The competition curves are shown in FIG. 6, and the concentrations of mutants giving half-maximal inhibitory effects (IC50 values) are listed in Table III.

TABLE III

Binding properties of IL-15 mutants on the TF-1 cell line.

| FLAG-IL-15 proteins | IC50 (pM) | relative activity (% WT) |
|---|---|---|
| WT | 23.6 | 100 |
| E46K | NA | NA |
| L69R | 9.1 | 259 |

WT, wild type.
NA, not applicable.

FLAG-IL-15 inhibited labelled rIL-15 binding with an IC50 of 23.6 pM. Mutation at position Leu-69 resulted in a slightly increased affinity of IL-15 (IC50=9.1 nM) in this competition assay.

Figure 7:
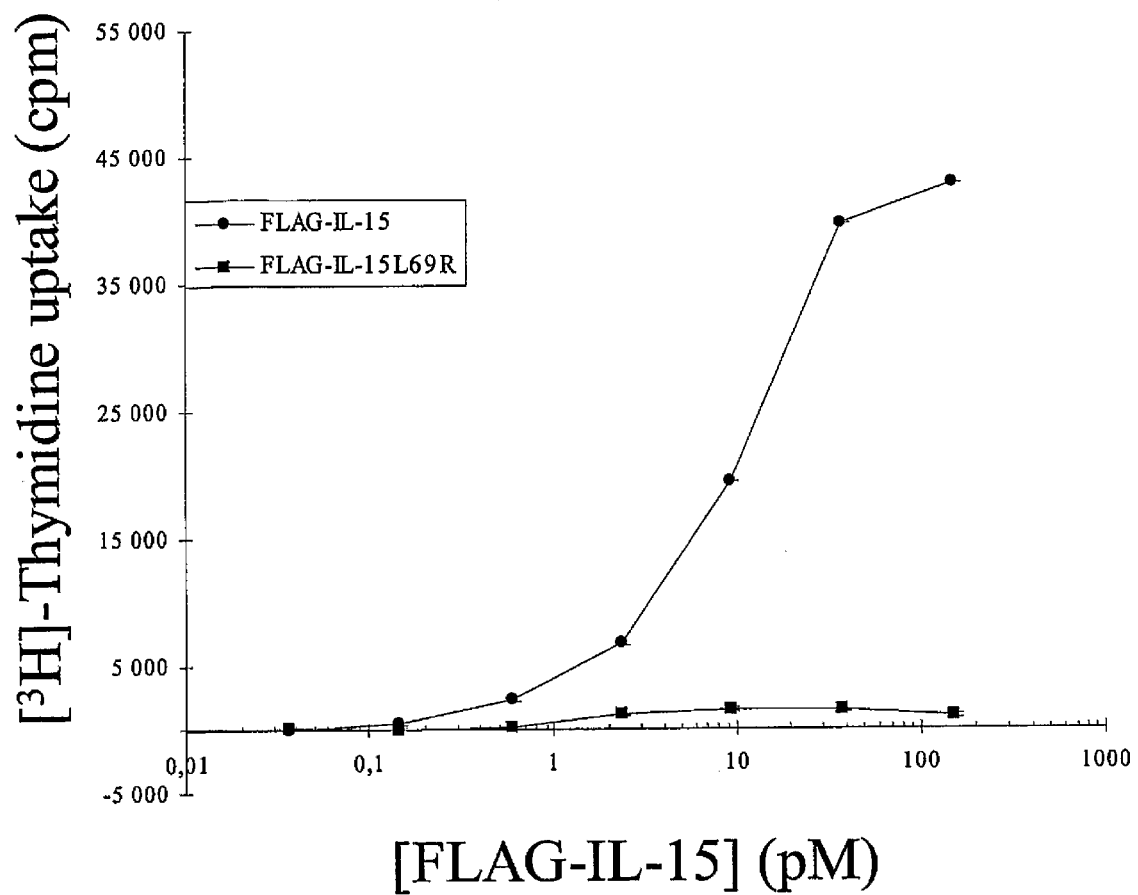
FIG. 7 illustrates the proliferative activities of Flag-IL-15 and mutants on TF-1β cells. TF-1β cells were cultured in the presence of increasing concentrations of FLAG-IL-15 wild type or mutant (L69R). Cell proliferation was evaluated by measuring the incorporation of [3H]thymidine. The standard deviations are low and they are hidden by the symbols.

Mutants were then tested for their growth-promoting effects on the IL-15-responsive TF-1β cells (FIG. 7). The L69R mutant behaved as a partial agonist on TF-1β with a maximal response being about 2% that of wild-type IL-15.

Inhibition by Flag-IL-15N65K of IL-15 induced TF1β proliferation in the presence of A41. Expression of the 3 receptor chains IL-15Rα, IL-2Rβ and $\gamma_c$ on the cell membrane allows to obtain a high affinity response to IL-15. Expression of both receptor chains IL-2Rβ and $\gamma_c$ allows to obtain an intermediate affinity proliferative response to IL-15. An anti IL-2Rβ mAb, A41, specifically blocking the IL-2Rβ/$\gamma_c$ receptor was used to block the IL-15 induced proliferation via the intermediate affinity receptor. The N65K affinity purified mutant of Flag-IL-15 produced a complete inhibition of IL-15 induced proliferation with an IC50 of 12 pM (FIG. 8), in correlation with its binding capacity to IL-15Rα on TF-1 cells (IC50=26.6 pM). The cell proliferation was totally inhibited at 100 pM.

Discussion:

The results of mutagenesis in the peptide 2/2a region showed that among the six amino acids evaluated (Glu-64 to Leu-69), mutants E64K, I68D and L69R had binding affinities to IL-15Rα at least similar to that of wild-type IL-15. However, the mutants behaved as partial agonists in the proliferation assay. Because partial agonism is indicative of defective activation of the receptor, Glu-64, Ile-68 and L69R might be involved in the recruitment of the IL-2R/β/$\gamma_c$ transduction complex.

This conclusion might hold for Asn-65 whose mutation (N65K) resulted in a loss of bio-activity without detectable alteration of the IL-15Rα binding affinity.

Our results suggest that regions in human IL-15 helix C, especially residues Glu-64, Asn-65, Ile-68 and L69R, participate in the recruitment of the IL-2Rβ chain.

The IL-15 mutants E64K, N65K, I68D and L69R display properties (low or no biological activity despite high affinity binding to IL-15Rα) that designate them as IL-15 antagonists (N65K) or partial agonists (E64K, I68D, L69R). The results shown in FIG. 8 indicate that N65K can totally inhibit high affinity IL-15-induced cell proliferation.

Footnotes

The abbreviations used are: IL, interleukin; rIL, recombinant IL; IL-15Rα, IL-15 receptor cc chain; NK, Natural Killer; Jak, Janus kinase; Stat, signal transducer and activator of transcription; Lck, lymphocyte specific tyrosine kinase; syk, Spleen tyrosine kinase; MAP, mitogen activated protein kinase; Bcl, B cell leukemia; GM-CSF, Granulocyte-Macrophage colony stimulating factor; mAb, monoclonal antibody; ELISA, enzyme-linked immunosorbent assay; RIA, radio-immuno assay; PCR, polymerase chain reaction; Dhfr, dihydrofolate reductase; IC50, inhibitory concentration 50%; EC50, effective concentration 50%; SP, signal peptide; PPL, preprolactine.

REFERENCES

1. Grabstein, K. H., Eisenman, J., Shanebeck, K., Rauch, C., Srinivasan, S., Fung, V., Beers, C., Richardson, J., Schoenborn, M. A., Ahdieh, M., Johnson, L., Alderson, M. R., Watson, J. D., Anderson, D. M., and Giri, J. G. (1994) *Science* 264, 965-968
2. Burton, J. D., Bamford, R. N., Peters, C., Grant, A. J., Kurys, G., Goldman, C. K., Brennan, J., Roessler, E., and Waldmann, T. A. (1994) *Proc. Natl. Acad. Sci. U.S.A.* 91, 4935-4939
3. Sprang, S. R., and Bazan, J. F. (1993) *Cur. Op. Struct. Biol.* 3, 815-827
4. Carson, W. E., Giri, J. G., Lindeman, M. J., Linett, M. L., Ahdieh, M., Paxton, R., Anderson, D., Eisenmann, J., Grabstein, K., and Caligiuri, M. A. (1994) *J. Exp. Med.* 180, 1395-1403
5. Armitage, R. J., Macduff, B. M., J., E., Paxton, R., and Grabstein, K. H. (1995) *J. Immunol.* 154, 483-490
6. Wilkinson, P. C., and Liew, F. Y. (1995) *J. Exp. Med.* 181, 1255-1259
7. Giri, J. G., Ahdieh, M., Eisenman, J., Shanebeck, K., Grabstein, K. H., Kumaki, A., Namen, A., Park, L. S., Cosman, D., and Anserson, D. M. (1994) *EMBO J.* 13, 2822-2830
8. Anderson, D. M., Kumaki, S., Ahdieh, M., Bertles, J., Tometsko, M., Loomis, A., Giri, J., Copeland, N. G., Gilbert, D. J., Jenkins, N. A., Valentine, V., Shapiro, D. N., Morris, S. W., Park, L. S., and Cosman, D. (1995) *J. Biol. Chem.* 270, 29862-29869
9. Norman, D. G., Barlow, P. N., Baron, M., Day, A. J., Sim, R. B., and Campbell, I. D. (1991) *J. Mol. Biol.* 219, 717-725
10. Minami, Y., Kono, T., Miyasaki, T., and Taniguchi, T. (1993) *Annu. Rev. Immunol.* 11, 245-267
11. Giri, J. G., Anderson, D. M., Kumaki, S., Park, L. S., Grabstein, K. H., and Cosman, D. (1995) *J. Leukoc. Biol.* 5745, 763-766
12. Lehours, P., Raher, S., Dubois, S., Guo, J., Godard, A., and Jacques, Y. (2000) *Eur. Cytokine Netw.* 11, 207-215
13. Johnston, J. A., Bacon, C. M., Finbloom, D. S., Rees, R. C., Kaplan, D., Shibuya, K., Ortaldo, J. R., Gupta, S., Chen, Y. Q., Giri, J. D., and O'Shea, J. J. (1995) *Proc. Natl. Acad. Sci. U.S.A.* 92, 8705-8709
14. Miyasaki, T., Liu, Z.-J., Kawahara, A., Minami, Y., Yamada, K., Tsujimoto, Y., Barsoumian, E. L., Perlmutter, R. M., and Taniguchi, T. (1995) *Cell* 81, 223-231
15. Bulanova, E., Budagian, V., Pohl, T., Krause, H., Durkop, H., Paus, R., and Bulfone-Paus, S. (2001) *J. Immunol.* 167, 6292-6302
16. Pereno, R., Giron-Michel, J., Gaggero, A., Cazes, E., Meazza, R., Monetti, M., Monaco, E., Mishal, Z., Jasmin, C., Indiveri, F., Ferrini, S., and Azzarone, B. (2000) *Oncogene* 19, 5153-5162
17. Bulfone-Paus, S. S., Bulanova, E., Pohl, T., Budagian, V., Durkop, H., Ruckert, R., Kunzendorf, U., Paus, R., and Krause, H. (1999) *Faseb J.* 13, 1575-1585
18. Stevens, A. C., Matthews, J., Andres, P., Baffis, V., Zheng, X. X., Chae, D. W., Smith, J., Strom, T. B., and Maslinski, W. (1997) *Am. J. Physiol.* 272, G1201-1208
19. Kennedy, M. K., Glaccum, M., Brown, S, N., Butz, E. A., Viney, J. L., Embers, M., Matsuki, N., Charrier, K., Sedger, L., Willis, C. R., Brasel, K., Morrissey, P. J., Stocking, K., Schuh, J. C., Joyce, S., and Peschon, J. J. (2000) *J. Exp. Med.* 191, 771-780
20. Lodolce, J. P., Burkett, P. R., Boone, D. L., Chien, M., and Ma, A. (2001) *J. Exp. Med.* 194, 1187-1194
21. Li, X. C., Demirci, G., Ferrari-Lacraz, S., Groves, C., Coyle, A., Malek, T. R., and Strom, T. B. (2001) *Nat. Med.* 7, 114-118
22. Fehniger, T. A., and Caligiuri, M. A. (2001) *Blood* 97, 14-32
23. Fehniger, T. A., Cooper, M. A., and Caligiuri, M. A. (2002) *Cytokine Growth Factor Rev.* 13, 169-183

24. Collins, L., Tsien, W. H., Seals, C., Hakimi, J., Weber, D., Bailon, P., Hoskings, J., Greene, W. C., Toome, V., and Ju, G. (1988) *Proc. Natl. Acad. Sci. U.S.A.* 85, 7709-7713
25. Sauve, K., Nachman, M., Spence, C., Bailon, P., Campbell, E., Tsien, W. H., Kondas, J. A., Hakimi, J., and Ju, G. (1991) *Proc. Natl. Acad. Sci. U.S.A.* 88, 4636-4640
26. Shanafelt, A. B., Lin, Y., Shanafelt, M. C., Forte, C. P., Dubois-Stringfellow, N., Carter, C., Gibbons, J. A., Cheng, S. L., Delaria, K. A., Fleischer, R., Greve, J. M., Gundel, R., Harris, K., Kelly, R., Koh, B., Li, Y., Lantz, L., Mak, P., Neyer, L., Plym, M. J., Roczniak, S., Serban, D., Thrift, J., Tsuchiyama, L., Wetzel, M., Wong, M., and Zolotorev, A. (2000) *Nat. Biotechnol.* 18, 1197-1202
27. Zurawski, S. M., Vega, F. J., Doyle, E. L., Huyghe, B., Flaherty, K., McKay, D. B., and Zuravski, G. (1993) *EMBO J.* 12, 5113-5119
28. Pettit, D. K., Bonnert, T. P., Eisenmnan, J., Srinivasan, S., Paxton, R., Beers, C., Lynch, D., Miller, B., Yost, J., Grabstein, K. H., and Gombotz, W. R. (1997) *J. Biol. Chem.* 272, 2312-2318
29. Farner, N. L., Gan, J., de Jong, J. L., Leary, T. P., Fenske, T. S., Buckley, P., Dunlap, S., and Sondel, P. M. (1997) *Cytokine* 9, 316-327
30. Weiss, A., Wiskocil, R. L., and Stobo, J. D. (1984) *J. Immunol.* 133, 123-128.
31. Matrisian, L. N., Bowden, G. T., Krieg, P., Fürstenberger, G., Briand, J. P., Leroy, P., and Breathnach, R. (1986) *Proc. Natl. Acad. Sci. U.S.A.* 83, 9413-9417
32. Blanc, C., Vusio, P., Schleinkofer, K., Boisteau, O., Pflanz, S., Minvielle, S., Grotzinger, J., Muller-Newen, G., Heinrich, P. C., Jacques, Y., and Montero-Julian, F. A. (2000) *J. Immunol. Methods* 241, 43-59
33. Slootstra, J. W., Puijk, W. C., Ligtvoet, G. J., Langeveld, J. P., and Meloen, R. H. (1996) *Mol. Divers.* 1, 87-96
34. Tejedor, F., and Ballesta, J. P. G. (1982) *Anal. Biochem.* 127, 143-149
35. Greene, W. C., Robb, R. J., Svetlick, P. B., Rusk, C. M., Depper, J. M., and Leonard, W. J. (1985) *J. Exp. Med.* 162, 363-368
36. Chang, D. Z., Wu, Z., and Ciardelli, T. L. (1996) *J. Biol. Chem.* 271, 13349-13355
37. Black, J. (1989) *Science* 139, 1550-1556
38. Bamborough, P., Hedgecock, C. J., and Richards, W. G. (1994) *Structure* 2, 839-851

---

The invention claimed is:

1. An IL-15 mutein, characterized in that it has a sequence that is directly derived from human mature wild-type IL-15 by one amino acid substitution within the region spanning from residue 44 to residue 52, or from residue 64 to residue 68, or from residue 64 to residue 69, this residue numbering corresponding to the human mature wild-type IL-15, provided that the IL-15 mutein resulting therefrom has an affinity for binding to IL-15Ralpha that is either not different from, or higher than the affinity of human mature wild-type IL-15 for binding to IL-15Ralpha.

2. The IL-15 mutein according to claim 1, characterized in that said one substitution is a substitution of L45, Q48, S51, L52, E64, N65, I68 or L69.

3. The IL-15 mutein according to claim 1, characterized in that it has a sequence that is directly derived from human mature wild-type IL-15 by one substitution within the region spanning from residue 44 to residue 52, this residue numbering corresponding to the human mature wild-type IL-15, provided that the IL-15 mutein resulting therefrom has an affinity for binding to IL-15Ralpha that is either not different from, or higher than the affinity of human mature wild-type IL-15 for binding to IL-15Ralpha, wherein said IL-15 mutein is an IL-15 agonist.

4. The IL-15 mutein according to claim 3, characterized in that said one substitution is a substitution of L45, Q48, S51 or L52.

5. The IL-15 mutein according to claim 3, characterized in that said one substitution is a substitution of L45, L52, S51, or Q48 by D, E, or K.

6. The IL-15 mutein according to claim 3, characterized in that said one substitution is a substitution of one of residues L45, S51, and L52.

7. The IL-15 mutein according to claim 3, characterized in that said one substitution is a substitution of residue L45 by D or E.

8. The IL-15 mutein according to claim 3, characterized in that said one substitution is a substitution of residue S51 by D.

9. The IL-15 mutein according to claim 3, characterized in that said one substitution is a substitution of residue L52 by D.

10. A pharmaceutical composition which comprises an IL-15 mutein according to claim 3 and at least one of a pharmaceutically acceptable vehicle, a pharmaceutically acceptable carrier, a pharmaceutically acceptable diluent, and a pharmaceutically acceptable adjuvant.

11. The IL-15 mutein according to claim 1, characterized in that it has a sequence that is directly derived from human mature wild-type IL-15 by one substitution within the region spanning from residue 64 to residue 68, this residue numbering corresponding to the human mature wild-type IL-15, provided that the IL-15 mutein resulting therefrom has an affinity for binding to IL-15Ralpha that is either not different from, or higher than the affinity of human mature wild-type IL-15 for binding to IL-15Ralpha, wherein said IL-15 mutein is an IL-15 antagonist or an IL-15 partial antagonist.

12. The IL-15 mutein according to claim 11, characterized in that said one substitution is a substitution of E64 by K.

13. The IL-15 mutein according to claim 11, characterized in that said at substitution is a substitution of residue N65 by K.

14. The IL-15 mutein according to claim 11, characterized in that said one substitution is a substitution of residue I68 by D.

15. The IL-15 mutein according to claim 11, characterized in that said one substitution is a substitution of residue L69 by R.

* * * * *

SEQUENCE LISTING

<160> NUMBER OF SEQ ID NOS: 85

<210> SEQ ID NO 1
<211> LENGTH: 1496
<212> TYPE: DNA
<213> ORGANISM: Homo sapiens
<220> FEATURE:
<221> NAME/KEY: CDS
<222> LOCATION: (373)..(861)

<400> SEQUENCE: 1

```
gactccgggt ggcaggcgcc cggggaatc ccagctgact cgctcactgc cttcgaagtc    60
cggcgccccc cgggagggaa ctgggtggcc gcaccctccc ggctgcggtg gctgtcgccc   120
cccaccctgc agccaggact cgatggagaa tccattccaa tatatggcca tgtggctctt   180
tggagcaatg ttccatcatg ttccatgctg ctgctgacgt cacatggagc acagaaatca   240
atgttagcag atagccagcc catacaagat cgtattgtat tgtaggaggc atcgtggatg   300
gatggctgct ggaaaccccct tgccatagcc agctcttctt caatacttaa ggatttaccg   360
tggctttgag ta atg aga att tcg aaa cca cat ttg aga agt att tcc atc    411
              Met Arg Ile Ser Lys Pro His Leu Arg Ser Ile Ser Ile
                1               5                   10 cag tgc tac ttg tgt tta ctt cta aac agt cat ttt cta act gaa gct      459
Gln Cys Tyr Leu Cys Leu Leu Leu Asn Ser His Phe Leu Thr Glu Ala
     15                  20                  25 ggc att cat gtc ttc att ttg ggc tgt ttc agt gca ggg ctt cct aaa      507
Gly Ile His Val Phe Ile Leu Gly Cys Phe Ser Ala Gly Leu Pro Lys
 30                  35                  40                  45 aca gaa gcc aac tgg gtg aat gta ata agt gat ttg aaa aaa att gaa      555
Thr Glu Ala Asn Trp Val Asn Val Ile Ser Asp Leu Lys Lys Ile Glu
                 50                  55                  60 gat ctt att caa tct atg cat att gat gct act tta tat acg gaa agt      603
Asp Leu Ile Gln Ser Met His Ile Asp Ala Thr Leu Tyr Thr Glu Ser
             65                  70                  75 gat gtt cac ccc agt tgc aaa gta aca gca atg aag tgc ttt ctc ttg      651
Asp Val His Pro Ser Cys Lys Val Thr Ala Met Lys Cys Phe Leu Leu
```

```
                80                    85                    90
gag tta caa gtt att tca ctt gag tcc gga gat gca agt att cat gat     699
Glu Leu Gln Val Ile Ser Leu Glu Ser Gly Asp Ala Ser Ile His Asp
    95                  100                 105 aca gta gaa aat ctg atc atc cta gca aac aac agt ttg tct tct aat     747
Thr Val Glu Asn Leu Ile Ile Leu Ala Asn Asn Ser Leu Ser Ser Asn
110                 115                 120                 125 ggg aat gta aca gaa tct gga tgc aaa gaa tgt gag gaa ctg gag gaa     795
Gly Asn Val Thr Glu Ser Gly Cys Lys Glu Cys Glu Glu Leu Glu Glu
                130                 135                 140 aaa aat att aaa gaa ttt ttg cag agt ttt gta cat att gtc caa atg     843
Lys Asn Ile Lys Glu Phe Leu Gln Ser Phe Val His Ile Val Gln Met
145                 150                 155 ttc atc aac act tct tga ttgcaattga ttctttttaa agtgtttctg            891
Phe Ile Asn Thr Ser
            160 ttattaacaa acatcactct gctgcttaga cataacaaaa cactcggcat ttcaaatgtg   951 ctgtcaaaac aagttttttct gtcaagaaga tgatcagacc ttggatcaga tgaactctta 1011 gaaatgaagg cagaaaaatg tcattgagta atatagtgac tatgaacttc tctcagactt  1071 actttactca tttttttaat ttattattga aattgtacat atttgtggaa taatgtaaaa  1131 tgttgaataa aaatatgtac aagtgttgtt ttttaagttg cactgatatt ttacctctta  1191 ttgcaaaata gcatttgttt aagggtgata gtcaaattat gtattggtgg ggctgggtac  1251 caatgctgca ggtcaacagc tatgctggta ggctcctgcc agtgtggaac cactgactac  1311 tggctctcat tgacttcctt actaagcata gcaaacagag gaagaatttg ttatcagtaa  1371 gaaaaagaag aactatatgt gaatcctctt ctttatactg taatttagtt attgatgtat  1431 aaagcaactg ttatgaaata agaaattgc aataactggc aaaaaaaaaa aaaaaaaaaa   1491 aaaaa                                                              1496
```

<210> SEQ ID NO 2
<211> LENGTH: 162
<212> TYPE: PRT
<213> ORGANISM: Homo sapiens

<400> SEQUENCE: 2

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30

Val Phe Ile Leu Gly Cys Phe Ser Ala Gly Leu Pro Lys Thr Glu Ala
        35                  40                  45

Asn Trp Val Asn Val Ile Ser Asp Leu Lys Lys Ile Glu Asp Leu Ile
    50                  55                  60

Gln Ser Met His Ile Asp Ala Thr Leu Tyr Thr Glu Ser Asp Val His
65                  70                  75                  80

Pro Ser Cys Lys Val Thr Ala Met Lys Cys Phe Leu Leu Glu Leu Gln
                85                  90                  95

Val Ile Ser Leu Glu Ser Gly Asp Ala Ser Ile His Asp Thr Val Glu
            100                 105                 110

Asn Leu Ile Ile Leu Ala Asn Asn Ser Leu Ser Ser Asn Gly Asn Val
        115                 120                 125

Thr Glu Ser Gly Cys Lys Glu Cys Glu Glu Leu Glu Glu Lys Asn Ile
    130                 135                 140
```

```
Lys Glu Phe Leu Gln Ser Phe Val His Ile Val Gln Met Phe Ile Asn
145                 150                 155                 160

Thr Ser

<210> SEQ ID NO 3
<211> LENGTH: 27
<212> TYPE: DNA
<213> ORGANISM: Homo sapiens
<220> FEATURE:
<221> NAME/KEY: CDS
<222> LOCATION: (1)..(27)

<400> SEQUENCE: 3 ctc ttg gag tta caa gtt att tca ctt                               27
Leu Leu Glu Leu Gln Val Ile Ser Leu
1               5

<210> SEQ ID NO 4
<211> LENGTH: 9
<212> TYPE: PRT
<213> ORGANISM: Homo sapiens

<400> SEQUENCE: 4

Leu Leu Glu Leu Gln Val Ile Ser Leu
1               5

<210> SEQ ID NO 5
<211> LENGTH: 15
<212> TYPE: DNA
<213> ORGANISM: Homo sapiens
<220> FEATURE:
<221> NAME/KEY: CDS
<222> LOCATION: (1)..(15)

<400> SEQUENCE: 5 gaa aat ctg atc atc                                               15
Glu Asn Leu Ile Ile
1               5

<210> SEQ ID NO 6
<211> LENGTH: 5
<212> TYPE: PRT
<213> ORGANISM: Homo sapiens

<400> SEQUENCE: 6

Glu Asn Leu Ile Ile
1               5

<210> SEQ ID NO 7
<211> LENGTH: 9
<212> TYPE: PRT
<213> ORGANISM: Artificial Sequence
<220> FEATURE:
<223> OTHER INFORMATION: IL15 mutant

<400> SEQUENCE: 7

Leu Asp Glu Leu Gln Val Ile Ser Leu
1               5

<210> SEQ ID NO 8
<211> LENGTH: 9
<212> TYPE: PRT
<213> ORGANISM: Artificial Sequence
<220> FEATURE:
<223> OTHER INFORMATION: IL15 mutant

<400> SEQUENCE: 8
```

Leu Glu Glu Leu Gln Val Ile Ser Leu
1               5

<210> SEQ ID NO 9
<211> LENGTH: 9
<212> TYPE: PRT
<213> ORGANISM: Artificial Sequence
<220> FEATURE:
<223> OTHER INFORMATION: IL15 mutant

<400> SEQUENCE: 9

Leu Lys Glu Leu Gln Val Ile Ser Leu
1               5

<210> SEQ ID NO 10
<211> LENGTH: 9
<212> TYPE: PRT
<213> ORGANISM: Artificial Sequence
<220> FEATURE:
<223> OTHER INFORMATION: IL15 mutant

<400> SEQUENCE: 10

Leu Arg Glu Leu Gln Val Ile Ser Leu
1               5

<210> SEQ ID NO 11
<211> LENGTH: 9
<212> TYPE: PRT
<213> ORGANISM: Artificial Sequence
<220> FEATURE:
<223> OTHER INFORMATION: IL15 mutant

<400> SEQUENCE: 11

Leu Leu Glu Leu Gln Val Ile Asp Leu
1               5

<210> SEQ ID NO 12
<211> LENGTH: 9
<212> TYPE: PRT
<213> ORGANISM: Artificial Sequence
<220> FEATURE:
<223> OTHER INFORMATION: IL15 mutant

<400> SEQUENCE: 12

Leu Leu Glu Leu Gln Val Ile Glu Leu
1               5

<210> SEQ ID NO 13
<211> LENGTH: 9
<212> TYPE: PRT
<213> ORGANISM: Artificial Sequence
<220> FEATURE:
<223> OTHER INFORMATION: IL15 mutant

<400> SEQUENCE: 13

Leu Leu Glu Leu Gln Val Ile Lys Leu
1               5

<210> SEQ ID NO 14
<211> LENGTH: 9
<212> TYPE: PRT
<213> ORGANISM: Artificial Sequence
<220> FEATURE:
<223> OTHER INFORMATION: IL15 mutant

<400> SEQUENCE: 14

```
Leu Leu Glu Leu Gln Val Ile Arg Leu
1               5

<210> SEQ ID NO 15
<211> LENGTH: 9
<212> TYPE: PRT
<213> ORGANISM: Artificial Sequence
<220> FEATURE:
<223> OTHER INFORMATION: IL15 mutant

<400> SEQUENCE: 15

Leu Leu Glu Leu Gln Val Ile Ser Asp
1               5

<210> SEQ ID NO 16
<211> LENGTH: 9
<212> TYPE: PRT
<213> ORGANISM: Artificial Sequence
<220> FEATURE:
<223> OTHER INFORMATION: IL15 mutant

<400> SEQUENCE: 16

Leu Leu Glu Leu Gln Val Ile Ser Glu
1               5

<210> SEQ ID NO 17
<211> LENGTH: 9
<212> TYPE: PRT
<213> ORGANISM: Artificial Sequence
<220> FEATURE:
<223> OTHER INFORMATION: IL15 mutant

<400> SEQUENCE: 17

Leu Leu Glu Leu Gln Val Ile Ser Lys
1               5

<210> SEQ ID NO 18
<211> LENGTH: 9
<212> TYPE: PRT
<213> ORGANISM: Artificial Sequence
<220> FEATURE:
<223> OTHER INFORMATION: IL15 mutant

<400> SEQUENCE: 18

Leu Leu Glu Leu Gln Val Ile Ser Arg
1               5

<210> SEQ ID NO 19
<211> LENGTH: 5
<212> TYPE: PRT
<213> ORGANISM: Artificial Sequence
<220> FEATURE:
<223> OTHER INFORMATION: IL15 mutant

<400> SEQUENCE: 19

Lys Asn Leu Ile Ile
1               5

<210> SEQ ID NO 20
<211> LENGTH: 5
<212> TYPE: PRT
<213> ORGANISM: Artificial Sequence
<220> FEATURE:
<223> OTHER INFORMATION: IL15 mutant

<400> SEQUENCE: 20

Arg Asn Leu Ile Ile
```

```
<210> SEQ ID NO 21
<211> LENGTH: 5
<212> TYPE: PRT
<213> ORGANISM: Artificial Sequence
<220> FEATURE:
<223> OTHER INFORMATION: IL15 mutant

<400> SEQUENCE: 21

Glu Asp Leu Ile Ile
1               5

<210> SEQ ID NO 22
<211> LENGTH: 5
<212> TYPE: PRT
<213> ORGANISM: Artificial Sequence
<220> FEATURE:
<223> OTHER INFORMATION: IL15 mutant

<400> SEQUENCE: 22

Glu Glu Leu Ile Ile
1               5

<210> SEQ ID NO 23
<211> LENGTH: 5
<212> TYPE: PRT
<213> ORGANISM: Artificial Sequence
<220> FEATURE:
<223> OTHER INFORMATION: IL15 mutant

<400> SEQUENCE: 23

Glu Lys Leu Ile Ile
1               5

<210> SEQ ID NO 24
<211> LENGTH: 5
<212> TYPE: PRT
<213> ORGANISM: Artificial Sequence
<220> FEATURE:
<223> OTHER INFORMATION: IL15 mutant

<400> SEQUENCE: 24

Glu Arg Leu Ile Ile
1               5

<210> SEQ ID NO 25
<211> LENGTH: 5
<212> TYPE: PRT
<213> ORGANISM: Artificial Sequence
<220> FEATURE:
<223> OTHER INFORMATION: IL15 mutant

<400> SEQUENCE: 25

Glu Asn Leu Ile Asp
1               5

<210> SEQ ID NO 26
<211> LENGTH: 5
<212> TYPE: PRT
<213> ORGANISM: Artificial Sequence
<220> FEATURE:
<223> OTHER INFORMATION: IL15 mutant

<400> SEQUENCE: 26

Glu Asn Leu Ile Glu
1               5
```

<210> SEQ ID NO 27
<211> LENGTH: 5
<212> TYPE: PRT
<213> ORGANISM: Artificial Sequence
<220> FEATURE:
<223> OTHER INFORMATION: IL15 mutant

<400> SEQUENCE: 27

Glu Asn Leu Ile Lys
1               5

<210> SEQ ID NO 28
<211> LENGTH: 5
<212> TYPE: PRT
<213> ORGANISM: Artificial Sequence
<220> FEATURE:
<223> OTHER INFORMATION: IL15 mutant

<400> SEQUENCE: 28

Glu Asn Leu Ile Arg
1               5

<210> SEQ ID NO 29
<211> LENGTH: 114
<212> TYPE: PRT
<213> ORGANISM: Artificial Sequence
<220> FEATURE:
<223> OTHER INFORMATION: IL15 mutant

<400> SEQUENCE: 29

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Asp Glu Leu Gln
            35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 30
<211> LENGTH: 114
<212> TYPE: PRT
<213> ORGANISM: Artificial Sequence
<220> FEATURE:
<223> OTHER INFORMATION: IL15 mutant

<400> SEQUENCE: 30

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Glu Glu Leu Gln
            35                  40                  45

-continued

Val Ile Ser Leu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 31
<211> LENGTH: 114
<212> TYPE: PRT
<213> ORGANISM: Artificial Sequence
<220> FEATURE:
<223> OTHER INFORMATION: IL15 mutant

<400> SEQUENCE: 31

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Lys Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 32
<211> LENGTH: 114
<212> TYPE: PRT
<213> ORGANISM: Artificial Sequence
<220> FEATURE:
<223> OTHER INFORMATION: IL15 mutant

<400> SEQUENCE: 32

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Arg Glu Leu Gln
        35                  40                  45

Val Ile Ser Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 33
<211> LENGTH: 114
<212> TYPE: PRT
<213> ORGANISM: Artificial Sequence
<220> FEATURE:
<223> OTHER INFORMATION: IL15 mutant

<400> SEQUENCE: 33

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Asp Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 34
<211> LENGTH: 114
<212> TYPE: PRT
<213> ORGANISM: Artificial Sequence
<220> FEATURE:
<223> OTHER INFORMATION: IL15 mutant

<400> SEQUENCE: 34

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Glu Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 35
<211> LENGTH: 114
<212> TYPE: PRT
<213> ORGANISM: Artificial Sequence
<220> FEATURE:
<223> OTHER INFORMATION: IL15 mutant

<400> SEQUENCE: 35

Asn Trp Val Asn Val Ile Ser Asp Leu Lys Lys Ile Glu Asp Leu Ile
1               5                   10                  15

```
Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Lys Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 36
<211> LENGTH: 114
<212> TYPE: PRT
<213> ORGANISM: Artificial Sequence
<220> FEATURE:
<223> OTHER INFORMATION: IL15 mutant

<400> SEQUENCE: 36

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Arg Leu Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser
```

<210> SEQ ID NO 37
<211> LENGTH: 114
<212> TYPE: PRT
<213> ORGANISM: Artificial Sequence
<220> FEATURE:
<223> OTHER INFORMATION: IL15 mutant

<400> SEQUENCE: 37

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Asp Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80
```

-continued

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 38
<211> LENGTH: 114
<212> TYPE: PRT
<213> ORGANISM: Artificial Sequence
<220> FEATURE:
<223> OTHER INFORMATION: IL15 mutant

<400> SEQUENCE: 38

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Glu Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 39
<211> LENGTH: 114
<212> TYPE: PRT
<213> ORGANISM: Artificial Sequence
<220> FEATURE:
<223> OTHER INFORMATION: IL15 mutant

<400> SEQUENCE: 39

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Lys Glu Ser Gly Asp Ala Ser Ile His Asp Thr Val Glu
        50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 40
<211> LENGTH: 114
<212> TYPE: PRT
<213> ORGANISM: Artificial Sequence

```
<220> FEATURE:
<223> OTHER INFORMATION: IL15 mutant

<400> SEQUENCE: 40

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Arg Glu Ser Gly Asp Ala Ser Ile His Asp Thr Val Glu
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 41
<211> LENGTH: 114
<212> TYPE: PRT
<213> ORGANISM: Artificial Sequence
<220> FEATURE:
<223> OTHER INFORMATION: IL15 mutant

<400> SEQUENCE: 41

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Lys
    50                  55                  60

Asn Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 42
<211> LENGTH: 114
<212> TYPE: PRT
<213> ORGANISM: Artificial Sequence
<220> FEATURE:
<223> OTHER INFORMATION: IL15 mutant

<400> SEQUENCE: 42

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45
```

Val Ile Ser Leu Glu Ser Gly Asp Ala Ser Ile His Asp Thr Val Arg
            50                  55                  60

Asn Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 43
<211> LENGTH: 114
<212> TYPE: PRT
<213> ORGANISM: Artificial Sequence
<220> FEATURE:
<223> OTHER INFORMATION: IL15 mutant

<400> SEQUENCE: 43

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
            50                  55                  60

Asp Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 44
<211> LENGTH: 114
<212> TYPE: PRT
<213> ORGANISM: Artificial Sequence
<220> FEATURE:
<223> OTHER INFORMATION: IL15 mutant

<400> SEQUENCE: 44

Asn Trp Val Asn Val Ile Ser Asp Leu Lys Lys Ile Glu Asp Leu Ile
 1               5                  10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
            50                  55                  60

Glu Leu Ile Ile Leu Ala Asn Asn Ser Leu Ser Ser Asn Gly Asn Val
 65                  70                  75                  80

Thr Glu Ser Gly Cys Lys Glu Cys Glu Glu Leu Glu Glu Lys Asn Ile
                 85                  90                  95

Lys Glu Phe Leu Gln Ser Phe Val His Ile Val Gln Met Phe Ile Asn
            100                 105                 110

Thr Ser

<210> SEQ ID NO 45
<211> LENGTH: 114
<212> TYPE: PRT
<213> ORGANISM: Artificial Sequence
<220> FEATURE:
<223> OTHER INFORMATION: IL15 mutant

<400> SEQUENCE: 45

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Lys Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 46
<211> LENGTH: 114
<212> TYPE: PRT
<213> ORGANISM: Artificial Sequence
<220> FEATURE:
<223> OTHER INFORMATION: IL15 mutant

<400> SEQUENCE: 46

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Arg Leu Ile Ile Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 47
<211> LENGTH: 114
<212> TYPE: PRT
<213> ORGANISM: Artificial Sequence
<220> FEATURE:
<223> OTHER INFORMATION: IL15 mutant

<400> SEQUENCE: 47

Asn Trp Val Asn Val Ile Ser Asp Leu Lys Lys Ile Glu Asp Leu Ile

```
                1               5                   10                  15
Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
                50                  55                  60

Asn Leu Ile Asp Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

<210> SEQ ID NO 48
<211> LENGTH: 114
<212> TYPE: PRT
<213> ORGANISM: Artificial Sequence
<220> FEATURE:
<223> OTHER INFORMATION: IL15 mutant

<400> SEQUENCE: 48

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
                50                  55                  60

Asn Leu Ile Glu Leu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser
```

<210> SEQ ID NO 49
<211> LENGTH: 114
<212> TYPE: PRT
<213> ORGANISM: Artificial Sequence
<220> FEATURE:
<223> OTHER INFORMATION: IL15 mutant

<400> SEQUENCE: 49

```
Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
                35                  40                  45

Val Ile Ser Leu Glu Ser Gly Asp Ala Ser Ile His Asp Thr Val Glu
                50                  55                  60

Asn Leu Ile Lys Leu Ala Asn Asn Ser Leu Ser Ser Asn Gly Asn Val
65                  70                  75                  80
```

```
Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 50
<211> LENGTH: 114
<212> TYPE: PRT
<213> ORGANISM: Artificial Sequence
<220> FEATURE:
<223> OTHER INFORMATION: IL15 mutant

<400> SEQUENCE: 50

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Arg Leu Ala Asn Asn Ser Leu Ser Ser Asn Gly Asn Val
65                  70                  75                  80

Thr Glu Ser Gly Cys Lys Glu Cys Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 51
<211> LENGTH: 18
<212> TYPE: DNA
<213> ORGANISM: Artificial Sequence
<220> FEATURE:
<223> OTHER INFORMATION: IL-2Rbeta sense primer

<400> SEQUENCE: 51
gagagactgg atggaccc                                                 18

<210> SEQ ID NO 52
<211> LENGTH: 23
<212> TYPE: DNA
<213> ORGANISM: Artificial Sequence
<220> FEATURE:
<223> OTHER INFORMATION: IL-2Rbeta anti-sense primer

<400> SEQUENCE: 52
aagaaactaa ctcttaaaga ggc                                           23

<210> SEQ ID NO 53
<211> LENGTH: 20
<212> TYPE: DNA
<213> ORGANISM: Artificial Sequence
<220> FEATURE:
<223> OTHER INFORMATION: IL-2Ralpha sense primer

<400> SEQUENCE: 53
agtccagcgg tgtcctgtgg                                               20
```

<210> SEQ ID NO 54
<211> LENGTH: 20
<212> TYPE: DNA
<213> ORGANISM: Artificial Sequence
<220> FEATURE:
<223> OTHER INFORMATION: IL-2Ralpha anti-sense primer

<400> SEQUENCE: 54
tcataggtgg tgagagcagt                                          20

<210> SEQ ID NO 55
<211> LENGTH: 28
<212> TYPE: DNA
<213> ORGANISM: Artificial Sequence
<220> FEATURE:
<223> OTHER INFORMATION: IL-2 sense primer

<400> SEQUENCE: 55
aactgcaggc acctacttca agttctac                                 28

<210> SEQ ID NO 56
<211> LENGTH: 28
<212> TYPE: DNA
<213> ORGANISM: Artificial Sequence
<220> FEATURE:
<223> OTHER INFORMATION: IL-2 anti-sense primer

<400> SEQUENCE: 56
tcccccgggt caagtcagtg ttgagatg                                 28

<210> SEQ ID NO 57
<211> LENGTH: 27
<212> TYPE: DNA
<213> ORGANISM: Artificial Sequence
<220> FEATURE:
<223> OTHER INFORMATION: IL-15Ralpha-IL-2 sense primer

<400> SEQUENCE: 57
gggaagctta gtccagcggt gtcctgt                                  27

<210> SEQ ID NO 58
<211> LENGTH: 26
<212> TYPE: DNA
<213> ORGANISM: Artificial Sequence
<220> FEATURE:
<223> OTHER INFORMATION: IL-15Ralpha-IL-2 anti-sense primer

<400> SEQUENCE: 58
aactgcagag tggtgtcgct gtggcc                                   26

<210> SEQ ID NO 59
<211> LENGTH: 27
<212> TYPE: DNA
<213> ORGANISM: Artificial Sequence
<220> FEATURE:
<223> OTHER INFORMATION: sense primer for rat prepolactin signal peptide

<400> SEQUENCE: 59
ggggtaccat caccatgaac agccaag                                  27

<210> SEQ ID NO 60
<211> LENGTH: 27
<212> TYPE: DNA
<213> ORGANISM: Artificial Sequence
<220> FEATURE:
<223> OTHER INFORMATION: antisense primer for rat preprolactin signal
     peptide

```
<400> SEQUENCE: 60
cgggatccgg tctgcacatt ttggcag                                          27

<210> SEQ ID NO 61
<211> LENGTH: 28
<212> TYPE: DNA
<213> ORGANISM: Artificial Sequence
<220> FEATURE:
<223> OTHER INFORMATION: sense primer for mature human IL-15

<400> SEQUENCE: 61
cgggatccaa ctgggtgaat gtaataag                                         28

<210> SEQ ID NO 62
<211> LENGTH: 26
<212> TYPE: DNA
<213> ORGANISM: Artificial Sequence
<220> FEATURE:
<223> OTHER INFORMATION: antisense primer for mature human IL-15

<400> SEQUENCE: 62
ggaattctca agaagtgttg atgaac                                           26

<210> SEQ ID NO 63
<211> LENGTH: 8
<212> TYPE: PRT
<213> ORGANISM: Artificial Sequence
<220> FEATURE:
<223> OTHER INFORMATION: FLAG tag

<400> SEQUENCE: 63

Asp Tyr Lys Asp Asp Asp Asp Lys
1               5

<210> SEQ ID NO 64
<211> LENGTH: 30
<212> TYPE: DNA
<213> ORGANISM: Artificial Sequence
<220> FEATURE:
<223> OTHER INFORMATION: FLAG tag oligo

<400> SEQUENCE: 64
gatcggacta caaggatgac gatgacaagc                                       30

<210> SEQ ID NO 65
<211> LENGTH: 30
<212> TYPE: DNA
<213> ORGANISM: Artificial Sequence
<220> FEATURE:
<223> OTHER INFORMATION: FLAG tag oligo

<400> SEQUENCE: 65
gatcgcttgt catcgtcatc cttgtagtcc                                       30

<210> SEQ ID NO 66
<211> LENGTH: 18
<212> TYPE: DNA
<213> ORGANISM: Homo sapiens

<400> SEQUENCE: 66
gaaaatctga tcatccta                                                    18

<210> SEQ ID NO 67
<211> LENGTH: 6
```

```
<212> TYPE: PRT
<213> ORGANISM: Homo sapiens

<400> SEQUENCE: 67

Glu Asn Leu Ile Ile Leu
1               5

<210> SEQ ID NO 68
<211> LENGTH: 6
<212> TYPE: PRT
<213> ORGANISM: Artificial Sequence
<220> FEATURE:
<223> OTHER INFORMATION: IL15 mutant

<400> SEQUENCE: 68

Lys Asn Leu Ile Ile Leu
1               5

<210> SEQ ID NO 69
<211> LENGTH: 6
<212> TYPE: PRT
<213> ORGANISM: Artificial Sequence
<220> FEATURE:
<223> OTHER INFORMATION: IL15 mutant

<400> SEQUENCE: 69

Arg Asn Leu Ile Ile Leu
1               5

<210> SEQ ID NO 70
<211> LENGTH: 6
<212> TYPE: PRT
<213> ORGANISM: Artificial Sequence
<220> FEATURE:
<223> OTHER INFORMATION: IL15 mutant

<400> SEQUENCE: 70

Glu Asp Leu Ile Ile Leu
1               5

<210> SEQ ID NO 71
<211> LENGTH: 6
<212> TYPE: PRT
<213> ORGANISM: Artificial Sequence
<220> FEATURE:
<223> OTHER INFORMATION: IL15 mutant

<400> SEQUENCE: 71

Glu Glu Leu Ile Ile Leu
1               5

<210> SEQ ID NO 72
<211> LENGTH: 6
<212> TYPE: PRT
<213> ORGANISM: Artificial Sequence
<220> FEATURE:
<223> OTHER INFORMATION: IL15 mutant

<400> SEQUENCE: 72

Glu Lys Leu Ile Ile Leu
1               5

<210> SEQ ID NO 73
<211> LENGTH: 6
<212> TYPE: PRT
<213> ORGANISM: Artificial Sequence
<220> FEATURE:
```

<223> OTHER INFORMATION: IL15 mutant

<400> SEQUENCE: 73

Glu Arg Leu Ile Ile Leu
1               5

<210> SEQ ID NO 74
<211> LENGTH: 6
<212> TYPE: PRT
<213> ORGANISM: Artificial Sequence
<220> FEATURE:
<223> OTHER INFORMATION: IL15 mutant

<400> SEQUENCE: 74

Glu Asn Leu Ile Asp Leu
1               5

<210> SEQ ID NO 75
<211> LENGTH: 6
<212> TYPE: PRT
<213> ORGANISM: Artificial Sequence
<220> FEATURE:
<223> OTHER INFORMATION: IL15 mutant

<400> SEQUENCE: 75

Glu Asn Leu Ile Glu Leu
1               5

<210> SEQ ID NO 76
<211> LENGTH: 6
<212> TYPE: PRT
<213> ORGANISM: Artificial Sequence
<220> FEATURE:
<223> OTHER INFORMATION: IL15 mutant

<400> SEQUENCE: 76

Glu Asn Leu Ile Lys Leu
1               5

<210> SEQ ID NO 77
<211> LENGTH: 6
<212> TYPE: PRT
<213> ORGANISM: Artificial Sequence
<220> FEATURE:
<223> OTHER INFORMATION: IL15 mutant

<400> SEQUENCE: 77

Glu Asn Leu Ile Ile Asp
1               5

<210> SEQ ID NO 78
<211> LENGTH: 6
<212> TYPE: PRT
<213> ORGANISM: Artificial Sequence
<220> FEATURE:
<223> OTHER INFORMATION: IL15 mutant

<400> SEQUENCE: 78

Glu Asn Leu Ile Ile Glu
1               5

<210> SEQ ID NO 79
<211> LENGTH: 6
<212> TYPE: PRT
<213> ORGANISM: Artificial Sequence
<220> FEATURE:
<223> OTHER INFORMATION: IL15 mutant

```
<400> SEQUENCE: 79

Glu Asn Leu Ile Ile Lys
1               5

<210> SEQ ID NO 80
<211> LENGTH: 6
<212> TYPE: PRT
<213> ORGANISM: Artificial Sequence
<220> FEATURE:
<223> OTHER INFORMATION: IL15 mutant

<400> SEQUENCE: 80

Glu Asn Leu Ile Ile Arg
1               5

<210> SEQ ID NO 81
<211> LENGTH: 6
<212> TYPE: PRT
<213> ORGANISM: Artificial Sequence
<220> FEATURE:
<223> OTHER INFORMATION: IL15 mutant

<400> SEQUENCE: 81

Glu Asn Leu Ile Arg Leu
1               5

<210> SEQ ID NO 82
<211> LENGTH: 114
<212> TYPE: PRT
<213> ORGANISM: Artificial Sequence
<220> FEATURE:
<223> OTHER INFORMATION: IL15 mutant

<400> SEQUENCE: 82

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
                20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
    50                  55                  60

Asn Leu Ile Ile Asp Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
                100                 105                 110

Thr Ser

<210> SEQ ID NO 83
<211> LENGTH: 114
<212> TYPE: PRT
<213> ORGANISM: Artificial Sequence
<220> FEATURE:
<223> OTHER INFORMATION: IL15 mutant

<400> SEQUENCE: 83

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
```

-continued

```
                 20                  25                  30

Pro Ser Cys Lys Val Thr Ala Met Lys Cys Phe Leu Leu Glu Leu Gln
            35                  40                  45

Val Ile Ser Leu Glu Ser Gly Asp Ala Ser Ile His Asp Thr Val Glu
        50                  55                  60

Asn Leu Ile Ile Glu Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 84
<211> LENGTH: 114
<212> TYPE: PRT
<213> ORGANISM: Artificial Sequence
<220> FEATURE:
<223> OTHER INFORMATION: IL15 mutant

<400> SEQUENCE: 84

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Lys Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95

Lys Glu Phe Leu Gln Ser Phe Val His Ile Val Gln Met Phe Ile Asn
            100                 105                 110

Thr Ser

<210> SEQ ID NO 85
<211> LENGTH: 114
<212> TYPE: PRT
<213> ORGANISM: Artificial Sequence
<220> FEATURE:
<223> OTHER INFORMATION: IL15 mutant

<400> SEQUENCE: 85

Asn Trp Val Asn Val Ile Ser Asp Leu Lys Lys Ile Glu Asp Leu Ile
1               5                   10                  15

Gln Ser Met His Ile Asp Ala Thr Leu Tyr Thr Glu Ser Asp Val His
            20                  25                  30

Pro Ser Cys Lys Val Thr Ala Met Lys Cys Phe Leu Leu Glu Leu Gln
        35                  40                  45

Val Ile Ser Leu Glu Ser Gly Asp Ala Ser Ile His Asp Thr Val Glu
    50                  55                  60

Asn Leu Ile Ile Arg Ala Asn Asn Ser Leu Ser Ser Asn Gly Asn Val
65                  70                  75                  80

Thr Glu Ser Gly Cys Lys Glu Cys Glu Glu Leu Glu Glu Lys Asn Ile
                85                  90                  95
```

```
Lys Glu Phe Leu Gln Ser Phe Val His Ile Val Gln Met Phe Ile Asn
            100                 105                 110
Thr Ser
```